(12) United States Patent
Hirota

(10) Patent No.: US 6,560,351 B1
(45) Date of Patent: May 6, 2003

(54) IMAGE READING APPARATUS CAPABLE OF DETECTING GLOSSINESS OF IMAGE SURFACE

(75) Inventor: Soh Hirota, Toyokawa (JP)

(73) Assignee: Minolta Co., Ltd., Osaka (JP)

( * ) Notice: Subject to any disclaimer, the term of this patent is extended or adjusted under 35 U.S.C. 154(b) by 0 days.

(21) Appl. No.: 09/354,108

(22) Filed: Jul. 15, 1999

(30) Foreign Application Priority Data

Jul. 17, 1998 (JP) .......................................... 10-203763

(51) Int. Cl.⁷ ................................................ G06K 9/00
(52) U.S. Cl. ....................................... 382/108; 356/369
(58) Field of Search ............................. 356/369, 364; 382/108, 111, 100, 312, 319, 325; 399/45; 250/209

(56) References Cited

U.S. PATENT DOCUMENTS

| | | | | |
|---|---|---|---|---|
| 5,162,860 A | * | 11/1992 | Nami et al. .................. | 355/327 |
| 5,552,890 A | * | 9/1996 | Nanna et al. ................. | 356/369 |
| 5,834,762 A | * | 11/1998 | Matsuda et al. .......... | 250/208.1 |
| 5,949,550 A | * | 9/1999 | Arndt et al. ................. | 356/430 |
| 6,088,546 A | * | 7/2000 | Inoue et al. .................. | 399/45 |

FOREIGN PATENT DOCUMENTS

| | | |
|---|---|---|
| JP | 06-070097 | 3/1994 |
| JP | 09-238237 | 9/1997 |

* cited by examiner

*Primary Examiner*—Yon J. Couso
(74) *Attorney, Agent, or Firm*—Burns, Doane, Swecker & Mathis, LLP

(57) ABSTRACT

In an image reading apparatus, an overall control portion can detect the glossiness of the image surface of an original using a sensor unit in producing image data. The user can set a condition to form an image in an operation panel. Overall control portion does not detect the glossiness of the image surface of an original with sensor unit in producing image data when a prescribed condition is set in operation panel.

8 Claims, 16 Drawing Sheets

F I G. 1
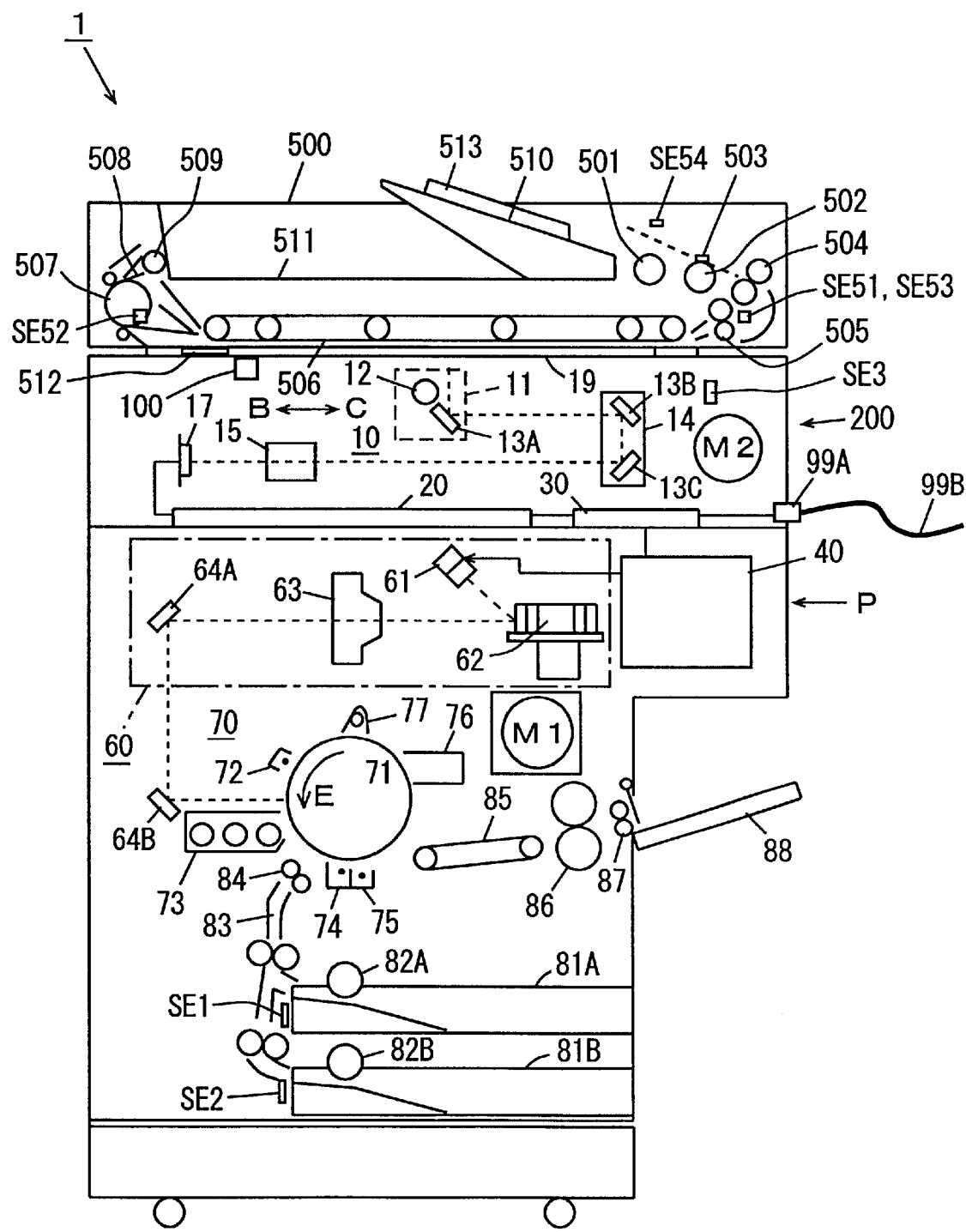

CHARACTER/PHOTOGRAPH MODE 1
Bk1=F911Bk (BK)

CHARACTER/PHOTOGRAPH MODE 2
Bk1=F912Bk (BK)

CHARACTER/PHOTOGRAPH MODE 3
Bk1=F913Bk (BK)

CHARACTER/PHOTOGRAPH MODE 4
Bk1=F914Bk (BK)

IMAGE READING APPARATUS CAPABLE OF DETECTING GLOSSINESS OF IMAGE SURFACE

This application is based on Application No. 10-203763 filed in Japan, the content of which is hereby incorporated by reference.

BACKGROUND OF THE INVENTION

1. Field of the Invention

The present invention relates generally to image reading apparatuses, and more particularly, to an image reading apparatus including glossiness detecting means for detecting the glossiness of the surface of an original image.

2. Description of the Related Art

A conventional image reading apparatus is for example disclosed by Japanese Patent Laying Open No. 6-70097. The image reading apparatus disclosed by this document reads image information and detects the glossiness of the image surface of an original. The image reading apparatus appropriately corrects read image information to produce image data if the detected glossiness is equal to or higher than a prescribed glossiness.

In the conventional image reading apparatus, a normal reflected light component and a regular reflection component from the image surface of an original are detected and the glossiness is detected based on the ratio of the detected components, irrespectively of normal reading of image information. Therefore, if the glossiness of the image surface is thus detected, a longer time period is necessary for producing the image data than otherwise.

In the conventional image reading apparatus which detects the glossiness of the image surface of the original, such detection of the glossiness is necessarily performed in any case. As a result, even if the glossiness of the image surface of an original is relatively low and the above described correction of image data is not necessary, it takes a long period of time to produce image data in the conventional apparatus.

SUMMARY OF THE INVENTION

Therefore, the present invention is in view of the above described circumstances and it is one object of the present invention is to provide an image reading apparatus which can produce appropriate image data irrespectively of the glossiness of the image surface of an original, and takes a shorter period of time as possible to produce image data.

Another object of the present invention is to provide image data according to the state of the image surface of an original.

According to one aspect of the present invention, the image reading apparatus includes glossiness detection portions for detecting the glossiness of the image surface of an original and control portions for prohibiting the operation of the glossiness detection portions.

By the image reading apparatus according to the present invention, the glossiness of the image surface of an original may be performed or may not be performed.

Therefore, the glossiness is detected if necessary while it is not detected if it is not necessary, so that the time required of producing data may be reduced.

The image reading apparatus preferably further includes input portions for setting image forming conditions, and the control portions prohibits the operation of the glossiness detection portions if a prescribed image condition is set in the input portions at the time of producing image data.

Thus, whether or not to detect the glossiness of the image surface of an original can be determined as the user desires.

The image reading apparatus further includes determination portions which determines an image mode based on the detection output of said glossiness detection portions and a set image forming condition, reads the image information of an original, and produces image data based on the image information and the image mode, and the determination portions determines one kind of image modes among at least three kinds of prescribed image modes based on the detection output.

Thus, image data more faithful to the state of the image surface of the original can be produced than the case of determining an image mode based on whether the glossiness is not less than a prescribed value.

The process of producing image data by the image reading apparatus preferably includes $\gamma$ correction or color correction, and the content of processing by $\gamma$ correction or color correction is changed when the image mode is changed according to the detection output of the glossiness detection portions.

Thus, the relation between the reflectance of light upon the surface of an original and the density of produced image data (reflectance-density characteristic) can be corrected. Note that the reflectance of light upon the surface of an original changes as the glossiness of the image surface of the original changes. As a result, image data more faithful to the state of the image surface of the original can be more effectively produced.

In the image reading apparatus, the control portions preferably prohibits the operation of the glossiness detection portions when the use of an automatic document feeder for transporting an original is set as an image forming condition.

Thus, if the use of the automatic feeder for transferring an original is set as an image forming condition, the glossiness of the image surface of the original is not detected. Note that the glossiness of the image surface of an original is usually low when such a condition is set.

Therefore, the image reading apparatus detects the glossiness of the image surface of an original when necessary, while automatically stop detecting the glossiness of an original if it is determined that the influence of the glossiness can be ignored in producing image data. As a result, time required for producing image data can be automatically reduced in this image reading apparatus.

The control portions preferably prohibits the operation of the glossiness detection portions when a condition about adjustment of the picture quality for image data to be produced is set as an image forming condition.

Thus, when a condition related to adjustment of the picture quality of image data to be produced is set as an image forming condition, the glossiness of the image surface of the original is not detected. Note that when such a condition is set, it is often the case that the user does not prefer the image to be automatically corrected by the machine.

Therefore, the image reading apparatus detects the glossiness when necessary, while automatically stops detecting the glossiness if it is determined that the influence of the glossiness can be ignored in producing image data. As a result, in the image reading apparatus, time required for producing image data can be automatically reduced.

In the image reading apparatus, the control portions makes non-detection control when the use of bound original sheets is set as an image forming condition.

Thus, when the use of bound original sheets is set as an image forming condition, the glossiness of the image surface of the original sheets will no longer be detected. Note that when such a condition is set, it is often the case that the glossiness of the image surface of the original sheets is low.

Therefore, the image reading apparatus automatically stops detecting the glossiness of the image surface of an original when it is determined that the glossiness of the image surface of the original is low and the influence of the glossiness can be ignored in producing image data. As a result, in the image reading apparatus, time required for producing image data can be automatically reduced.

According to another aspect of the present invention, the image reading apparatus includes glossiness detection portions which produces image data according to an image mode and detects the glossiness of the image surface of the original, control portions which prohibits the operation of the glossiness detection portions, and input portions which sets an image mode, and the control portions controls the operation of the glossiness detection portions based on the image mode set by the input portions.

Thus, the control portions can determine whether or not to detect the glossiness based on the input image mode.

As a result, the glossiness may be detected when necessary, while the glossiness is not detected in producing image data when detection of the glossiness is not necessary, so that time required for producing image data can be reduced.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a general front view of the internal structure of a copying machine including an image reading apparatus according to the present invention;

DESCRIPTION OF THE PREFERRED EMBODIMENTS

Figure 2:
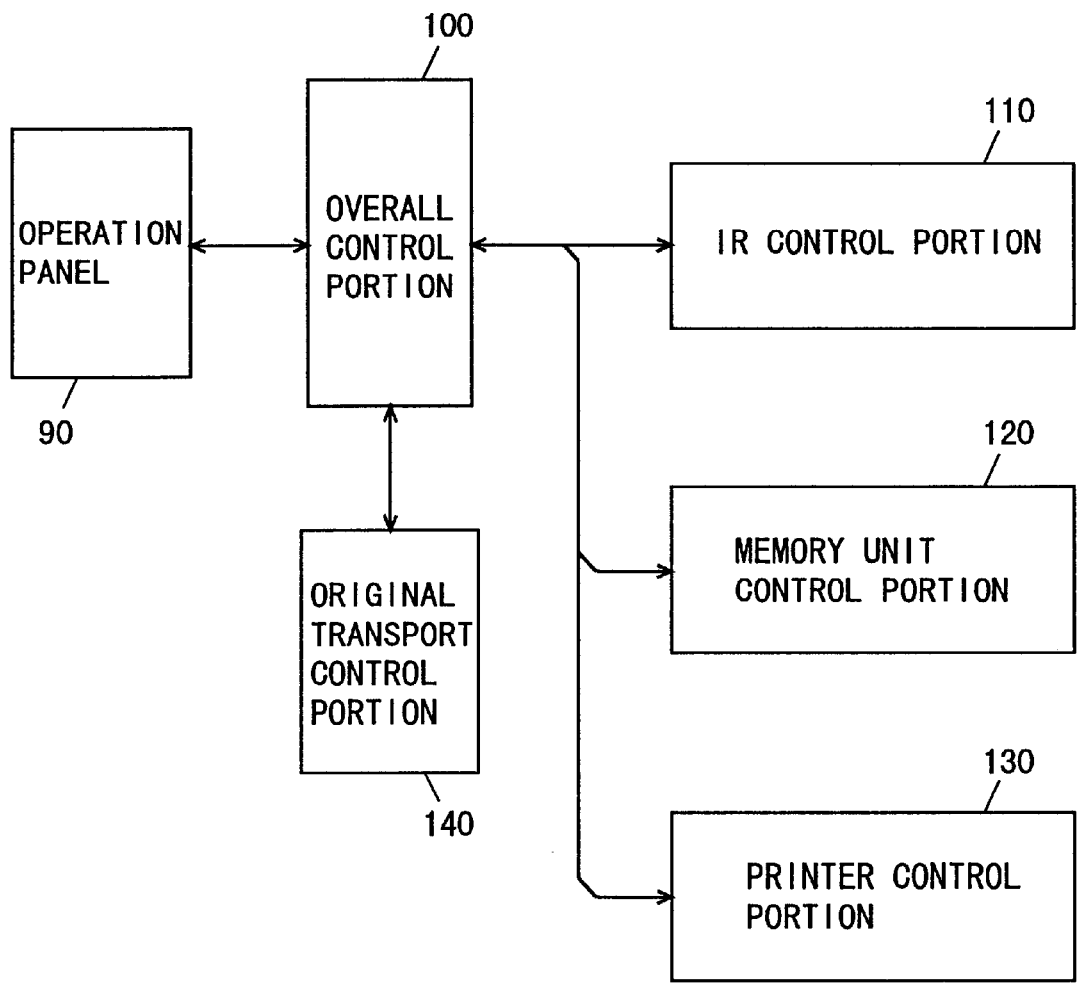
FIG. 2 is a block diagram of the entire block of the control system of the copying machine shown in FIG. 1.
Figure 9:
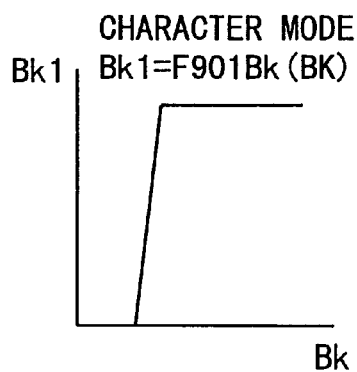
FIG. 9 is a graph showing an example of a transform function $F901Bk$ used in $\gamma$ correction to image data in the copying machine in FIG. 1.

An embodiment of the present invention will be now described in conjunction with the accompanying drawings.

1. General Structure of a Copying Machine

FIG. 1 is a cross sectional view of the general structure of a digital copying machine including an image reading apparatus according to the present invention.

In FIG. 1, copying machine 1 mainly includes a scanning system 10, an image processing unit 20, a memory unit 30, a printing processing unit 40, a laser optical system 60, an image forming system 70, an operation panel (not shown in FIG. 1), and an original transport portion 500. Scanning system 10 reads the image of an original and converts the read image into an image signal. Image processing unit 20 performs an appropriate processing to the image signal sent from scanning system 10. Memory unit 30 outputs the image data input from image processing unit 20 as is or after rotating to printing processing unit 40. Printing processing unit 40 drives a semiconductor laser 61 based on the imaged data output from memory unit 30. Laser optical system 60 guides a laser beam emitted from semiconductor laser 61 to an exposure position on a photoreceptor drum 71. Image forming system 70 develops a latent image by exposure for transfer onto a recording sheet, and an image is fixed and formed. The operation panel is provided on the upper surface of copying machine 1. Original transport portion 500 transports an original and reverses the front and back of the original if necessary. Memory unit 30 is connected to external equipment through an external device connecting connector 99A and a communication line 99B, such that copying machine 1 is connected to the external equipment. Copying machine 1 can form images based on image data input from the external equipment.

In copying machine 1, scanning system 10, image processing unit 20 and memory unit 30 form a reading portion 200. Printing processing unit 40, laser optical system 60 and image forming system 70 form a printer portion P.

Reading portion 200 reads an image on an original placed on a platen glass 19 and produces image data corresponding to pixels in the image of the original. In reading the image, a first scanner 11 having an exposure lamp 12 and a first mirror 13A, a second scanner 14 having second and third mirrors 13B and 13C are driven by a scan motor M2 to move in the directions denoted by arrows B and C (the sub scanning directions), respectively. Light emitted by exposure lamp 12 is reflected by the original on platen glass 19. The reflected light is directed upon a line sensor 17 through first to third mirrors 13A, 13B and 13C and a lens 15.

Line sensor 17 includes a large number of photoelectric conversion elements (CCDs) arranged in the direction orthogonal to the surface of the sheet of FIG. 1 (the main scanning direction). Line sensor 17 reads an image at 400 dpi and outputs image data corresponding to the pixels to image processing unit 20.

First scanner 11 is moved in the directions denoted by arrows B and C as described above and therefore line sensor 17 can scan the image on the original in the sub scanning direction.

A sensor SE3 is used to detect first scanner 11 being in the home position. A scan motor M2 moves first and second scanners 11 and 14 in the direction B faster than in the direction C. More specifically, scanning of an image by line sensor 17 when first and second scanners 11 and 14 move in the direction B is preliminary scanning. Meanwhile, scanning of an image by line sensor 17 when first and second scanners 11 and 14 move in the direction C is main scanning. The position of an original on platen glass 19 is detected based on image data output by line sensor 17 at the time of preliminary scanning. Copying machine 1 copies an image on an original based on an image output by line sensor at the time of main scanning.

Image data output from line sensor 17 is processed in image processing unit 20, and then sent to memory unit 30. Memory unit 30 temporarily stores the image data received from image processing unit 20 and transmits the data as is or after a rotation editing processing to printer portion P.

The operation of printer portion P will be now described. Printing processing unit 40 controls laser optical system 60 based on image data received from memory unit 30. Laser optical system 60 includes a semiconductor laser 61, a polygon mirror 62, fθ lens 63, and mirrors 64A and 64B. Polygon mirror 62 directs a laser beam emitted by semiconductor laser 61 upon photoreceptor drum 71 for scanning. The laser beam emitted by semiconductor laser 61 is modulated (turned on/off) under the control of printing unit 40.

Photoreceptor drum 71 is driven to rotate in the direction E. There are provided around photoreceptor drum 71 along the rotation direction (direction E) a corona charger 72, a developer 73, a transfer charger 74, a separation charger 75, a cleaner 76, and an eraser lamp 77. Using these elements, a toner image is formed by a well-known electrophotography process and transferred onto a sheet. The sheet is supplied form paper feeding cassettes 81A, 81B to a sheet transfer passage 83 by paper feeding rollers 82A, 82B, and sent to a position facing transfer charger 74 by a timing roller 84. The sheet is then transferred with a toner image at the position facing transfer charger 74 and then let out onto a paper discharge tray 88 through a transport belt 85, a fixing device 86, and a discharge roller 87. These various kinds of rollers and photoreceptor drum 71 are driven by main motor M1. Sheet size detection sensors SE1 and SE2 used to detect the size of sheets stored in paper feeding cassettes 81A, 81B are provided adjacent to the cassettes.

Original transport portion 500 automatically transports an original set on an original feeding tray 510 and discharges an original having its image read by scanning system 10 onto discharge tray 511.

The user normally sets a original sheet(s) on original feeding tray 510 with its image reading surface facing up, and adjusts side restriction plate 513 to the size of the original sheet. Thus, an empty sensor SE54 detects the presence of the original sheet on original feeding tray 510.

Copying machine 1 includes a sensor unit 600. Sensor unit 600 is provided under platen glass 19 in order to detect the state of the image surface of an original. Sensor unit 600 will be described later in detail.

When a copying operation is started in copying machine 1, original sheets set on original feeding tray 510 are transported by paper feeding roller 501 sequentially from the sheet on the bottom, separated by a separator roller 502 and a separator pad 503, and fed to an intermediate roller 504 on a sheet-basis. Each original sheet transported passes through intermediate roller 504, has its size detected by a resist sensor SE51 and a width size sensor SE53, and then has its direction adjusted by a resist roller 505. Then, the original sheet is transported on platen glass 19 by resist roller 505 and original transport belt 506, and immediately after having its tip end abutted against an original scale 512, original transport belt 506 and resist roller 505 are stopped.

Thus, the left end of the original sheet abuts against the edge of original scale 512 so that the original sheet can be set at a correct position on platen glass 19. At this time, the tip end of the next original sheet has reached resist roller 505. Thus, in copying machine 1, time required between the completion of reading of an original sheet and the start of reading of the next original sheet can be reduced.

When an original sheet is set at a correct position on platen glass 19, scanning to read the original sheet is performed by scanning system 10. When the reading of the original sheet completes, original scale 512 is pressed to a lower level than platen glass 19 by the function of a solenoid which is not shown. Thereafter, the original sheet is transported to the left in the sheet of the figure by original transport belt 506, and changed in the transport direction by an inversion roller 507, and passes above switching claw 508 to be discharged onto discharge tray 511.

The operation of original transport portion 500 when a "step feeding mode" is selected will be now described. If the size of an original sheet is half or less that of the length from the edge of original scale 512 to the nip position of resist roller 505, the preceding original sheet (the first sheet) is stopped at an exposure reference position, and the next original (the second sheet) is transported to the intermediate position between the edge of original scale 512 and the nip position of resist roller 505, and then the next original sheet (the third sheet) is transported until its tip end abuts against resist roller 505. Thus, the original sheets are transported step-wise by half the distance between the exposure reference position and resist roller 505, so that the time required for exchanging original sheets on platen glass 19 is reduced. More specifically, during the time period after exposure of an original (the first sheet) completes till scanning system 10 returns to its home position, the next original sheet (the second sheet) can be sent to the exposure reference position, so that the copying productivity can be improved. Furthermore, the succeeding original sheet (the third sheet) has been transferred until its tip end abuts against resist roller 505. The transport of the third sheet is performed during the exposure of the first original sheet, the copying productivity can be improved.

If an original sheet has images on both sides, a "both-sided mode" is selected. In this case, a first side is read and then the original sheet is transported to the left by original transport belt 506. Then, the original sheet has its transport direction changed by inversion roller 507, and then once again sent onto platen glass 19 by an appropriate movement of switching claw 508. Thus, the second surface of the original is set at the reading position. Re-sending sensor SE52 detects the original sheet at this time. Thus, a second side of the original sheet is set at the reading position. When the second side is read, the original sheet is transported to the left in the figure by original transport belt 506, and discharged onto discharge tray 511 through inversion roller 507, switching claw 508 and discharge roller 509.

Note that in the operation panel, when a mode such as "step feeding mode" and "both-sided mode" is selected, unlike the normal case, the transport of an original sheet by transport belt 506 is stopped immediately before the tip end of the original sheet abuts against the right end of original scale 512, and the original is set at a position slightly apart from original scale 512.

The face of original transport belt 506 facing platen glass 19 is colored Mars yellow. Thus, light emitted from exposure lamp 12 and reflected from original transport belt 506 has low spectroscopic sensitivity in color. More specifically, to line sensor 17, original transport belt 506 is practically in black. Meanwhile, the background of the original is normally white. Therefore, even with original transport belt 506 being closed, line sensor 17 can identify the original sheet from the lower surface of the original transport belt 506. If original transport portion 500 is not closed, light emitted from exposure lamp 12 and reflected from original transport belt 506 does not reach line sensor 17, the original region can be identified.

The general block diagram of the control system in copying machine 1 is shown in FIG. 2.

Referring to FIG. 2, the control system of copying machine 1 includes control portions including an IR control portion 110, a memory unit control portion 120, a printer control portion 130, and an original transport control portion 140. These portions are connected to overall control portion 100 by a communication line. Note that IR control portion 110 controls the operation of reading portion 200, memory unit control portion 120 controls the operation of memory unit 30, printer control portion 130 controls the operation of printer portion P, and original transport control portion 140 controls the operation of original transport portion 500. Overall control portion 100 exchanges data with the control portions and controls the operation panel 90 (see FIG. 3) as well.

Figure 3:
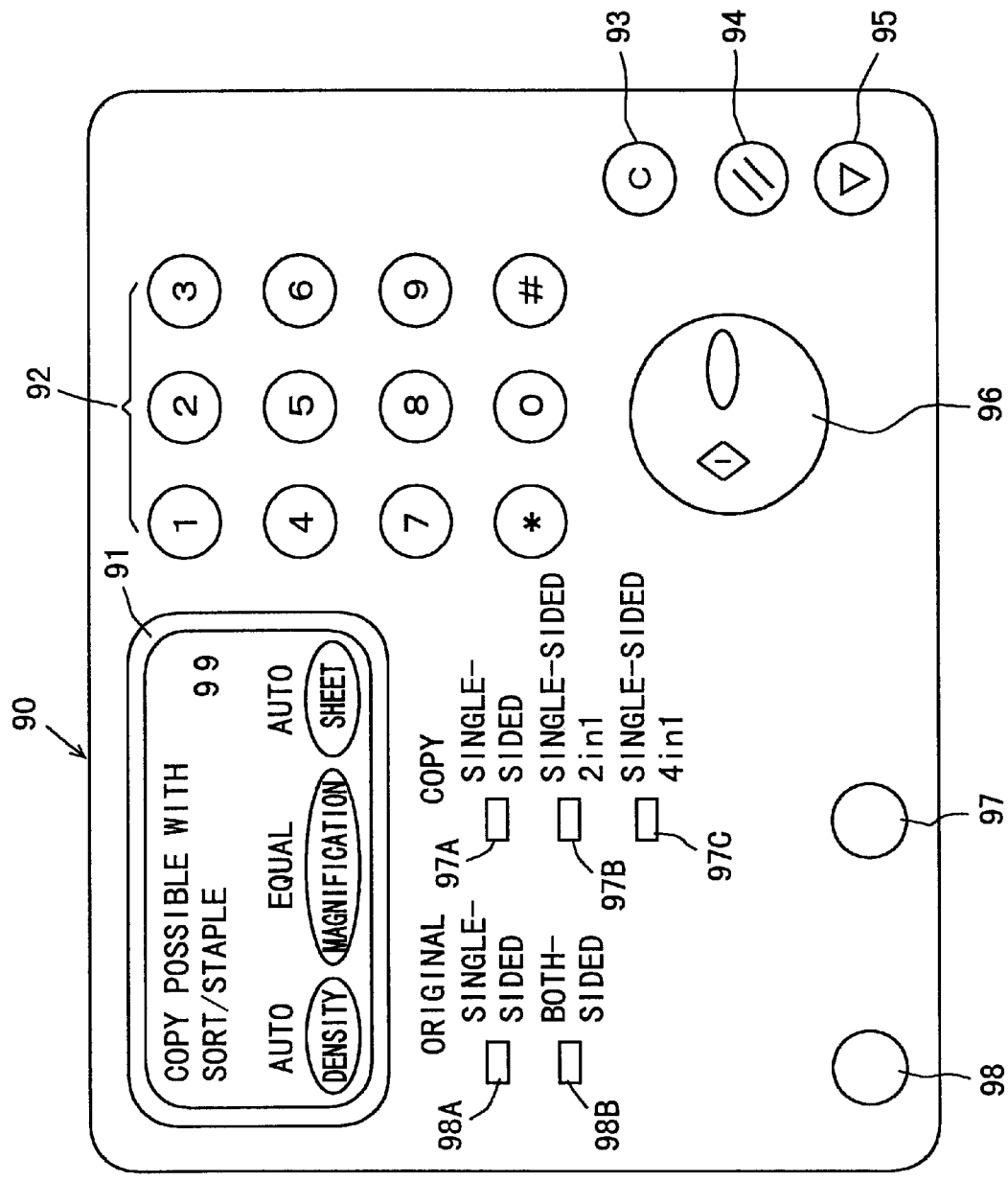
FIG. 3 is a plan view of the structure of the operation panel of the copying machine shown in FIG. 1.

FIG. 3 is a view showing operation panel 90 in copying machine 1.

Referring to FIG. 3, operation panel 90 includes an LCD touch panel 91, a ten-key 92, a clear key 93, a panel reset key 94, a stop key 95 and a start key 96. Ten-key 92 is used to input various numerals including the older of page numbers of original sheets, the number of copies needed and copy magnification. Clear key 93 is used to return an input numeral to a reference value "1". Panel reset key 94 is used to return a value set for copying machine 1 to a reference value. Stop key 95 is used to interrupt a copying operation, and start key 96 is used to start a copying operation.

Furthermore, operation panel 90 includes a copy mode setting key 97, an original mode setting key 98, indication portions 97A to 97C and indication portions 98A and 98B. Copy mode setting key 97 is used to set any of copy single-sided mode, single-sided 2 in 1 mode and single-sided 4 in 1 mode as a copy mode. Original mode setting key 98 is used to set one of original single-sided mode and original both-sided mode ("both-sided mode" as described above) as an original mode. When the copy single-sided mode is set as the copy mode, indication portion 97A indicates the mode, when the single-sided 2 in 1 mode is set, indication portion 97B indicates the mode, and when the single 4 in 1 mode is set, indication portion 97C indicates the mode. If the original single-sided mode is set as the original mode, indication portion 98A indicates the mode, while when the original both-sided mode is set, indication portion 98B indicates the mode.

LCD touch panel 91 displays various abnormal states in copying machine 1 and other kinds of information. The abnormal states in copying machine 1 herein include abnormalities in operation states related to for example the image mode, exposure level, copying magnification, recording sheet size, and editing function in copying machine 1, and occurrence of jam, serviceman call and paper empty. The user can input information to designate image forming conditions such as density, copying magnification and recording sheet through touch panel 91.

2. Control By the Control System of the Copying Machine

Figure 4:
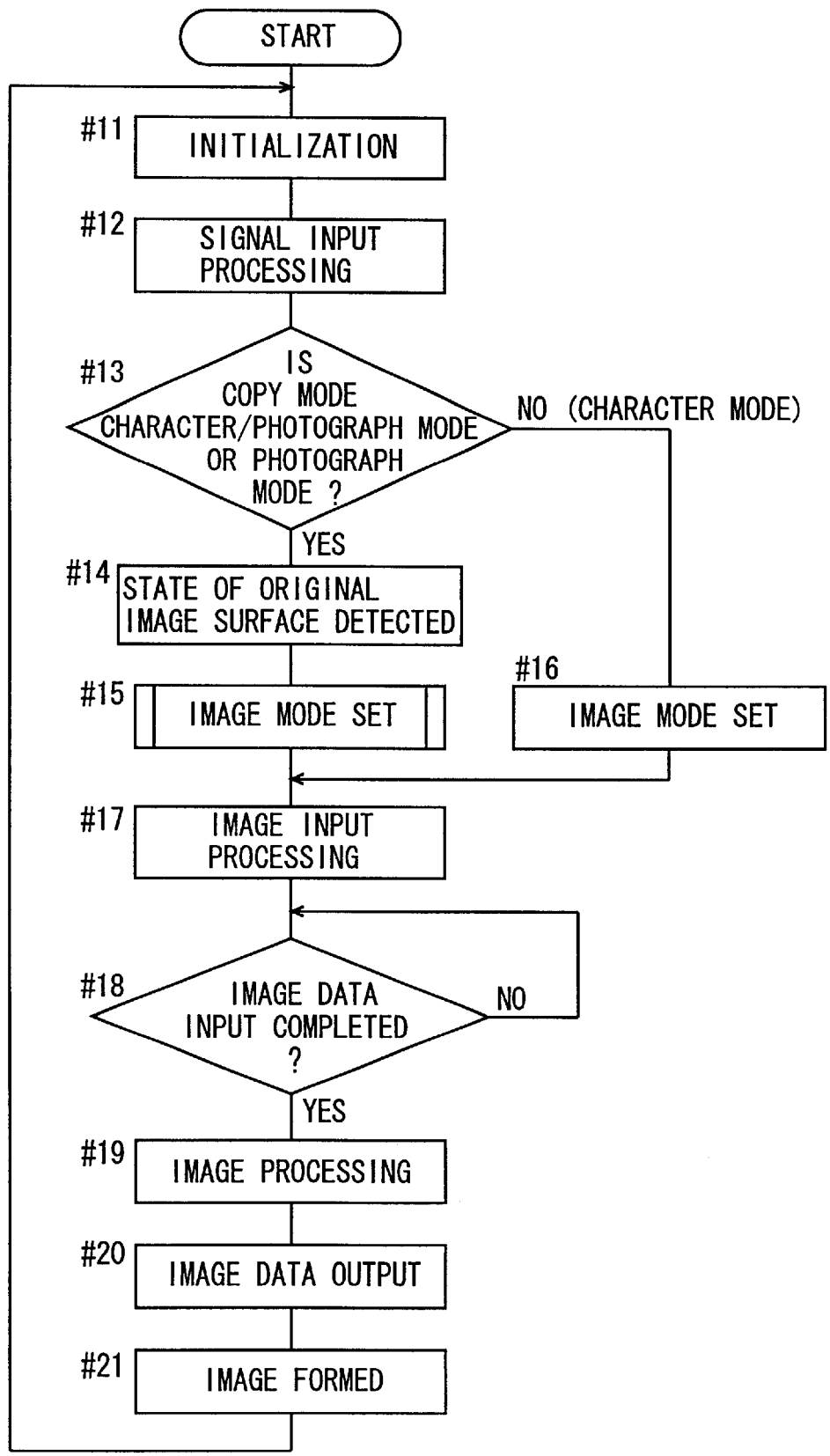
FIG. 4 is a flow chart for use in illustration of the processing content of the entire control portion which controls the operation of the copying machine in FIG. 1.

Referring to FIG. 4, the processing of overall control portion 100 which controls the overall operation of copying machine 1 will be now described.

When the power supply is activated, overall control portion 100 initializes a RAM or the like stored therein (#11). Then, a processing in response to input signals from various switches from operation panel 90 (#12). Thereafter, a copy start request is made through operation panel 90, and if the copy mode in the copying operation has been set to either "character/photograph mode" or "photograph mode" (Yes in #13), the control proceeds to #14. The copy mode herein is an example of image forming conditions set for the kind of the image of an original in copying machine 1, and there are three kinds of copy modes, "character/photograph mode", "photograph mode" and "character mode". In #14, the state of the image surface of the original is detected and the control proceeds to #15.

In #15, an image mode in consideration of the copy mode previously selected in operation panel 90 and the state of the image surface of the original is set.

Meanwhile, if the copy mode is neither "character/photograph mode" nor "photograph mode", in other words, if the copy mode set in operation panel 90 is the "character mode", the control proceeds to #16 from #13, the image mode is set to the "character mode", and the control proceeds to #17. The image mode herein is the kind of conversion to which image data is subjected to in an image processing in #19 which will be described. The image mode is determined by overall control portion 100 and the determined image mode is sent to memory unit control portion 120.

In #17, image data read by line sensor 17 is input to image processing unit 20. When input of the image data completes (Yes in #18), depending upon an image forming condition input to operation panel 90 or the image mode set in #17, image processings such as density conversion, color correction, γ correction and MTF correction are performed (#19), and the control proceeds to #20. In #20, image data is output from image processing unit 20 to printer portion P through memory unit 30, and an image is formed by printer portion P based on the image data (#21).

As described above, according to the process described in conjunction with FIG. 4, when the character mode is selected by operation panel 90 as the copy mode (No in #13), the step of detecting the state of the image surface of an original (#14) is omitted, and the image mode is set based on the copy mode. Thus, copying machine 1 will have the following characteristics.

More specifically, when the user selects the character mode as the copy mode, it is often the case that the glossiness of the image surface of the original is low. If the glossiness of the image surface of the original is low, correction according to the glossiness of the surface does not have to be performed to image information read by the CCD in the image processing step (#19). If the process to detect the state of the image surface of the original (#14) is performed, a sensor unit 600 must be operated separately from the CCD, and therefore a relatively long time period is necessary for producing image data. In copying machine 1 according to this embodiment, when the character mode is selected, more specifically, when correction according to the glossiness of the image surface is hardly necessary, the process of detecting the state of the image surface is automatically omitted. Therefore, appropriate image data can be produced irrespectively of the glossiness of the image surface of the original, while the time required for producing the image data can be reduced when correction according to the glossiness of the surface is not necessary.

3. Detection of the Glossiness of the Image Surface of an Original

Figure 5A:
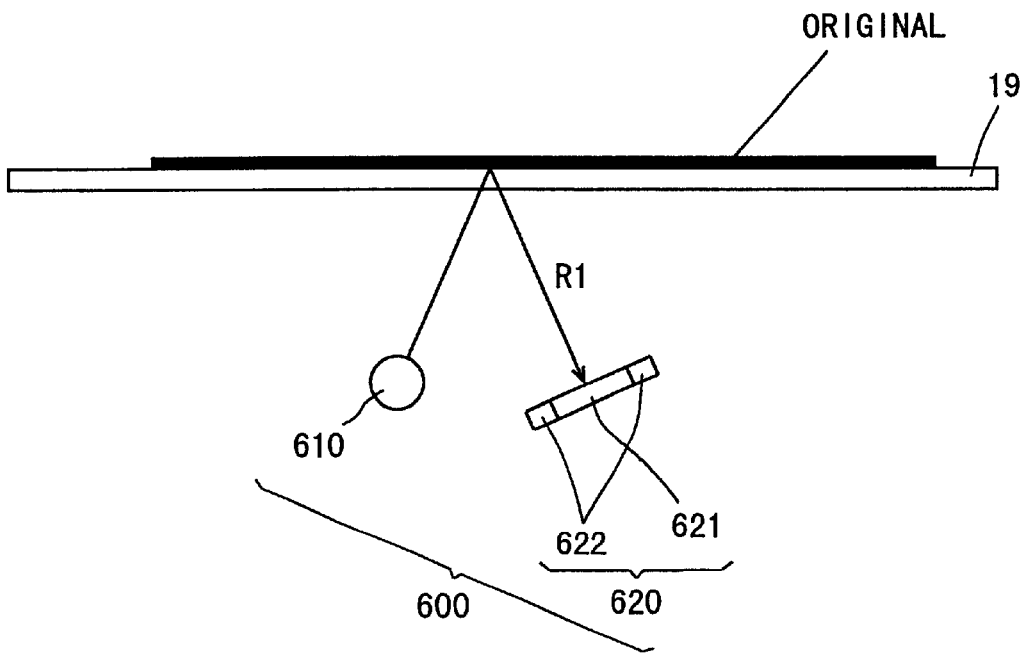
FIG. 5A is a diagram for use in illustration of how a sensor receives regular reflection light upon the image surface of an original in the copying machine in FIG. 1.
Figure 5B:
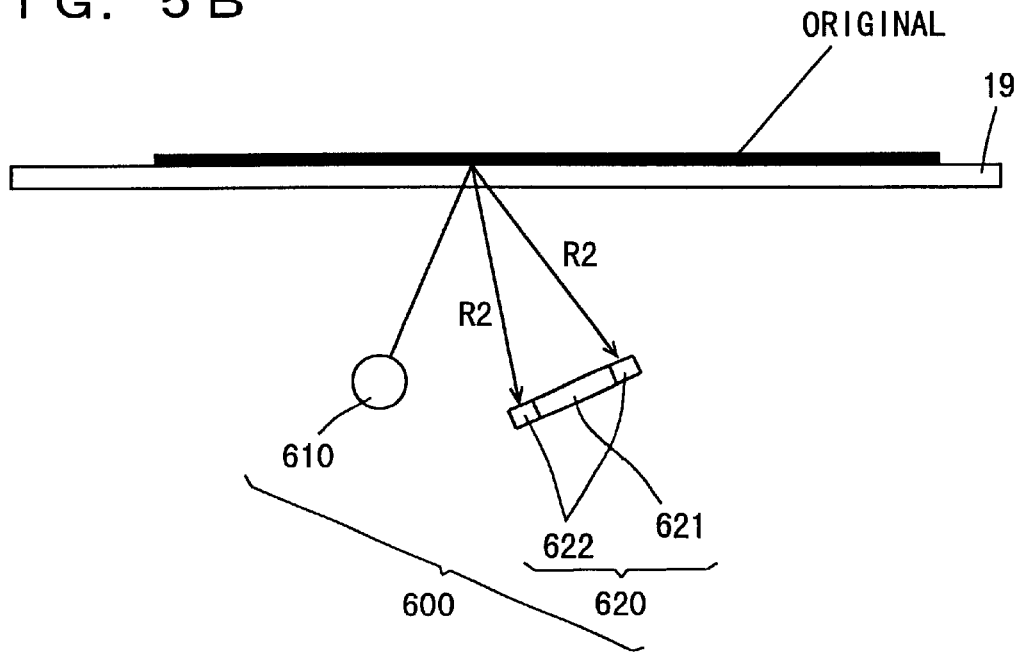
FIG. 5B is a diagram for use in illustration of how a sensor receives light diffusely reflected upon the image surface of an original in the copying machine in FIG. 1.

FIGS. 5A and 5B are diagrams showing an example of sensor unit 600 to actually detect the state (glossiness) of the image surface of the original in #14. Sensor unit 600 includes an optical source 610 and a sensor 620. Sensor 620 receives light emitted from optical source 610 and reflected from the image surface of an original. Sensor 620 includes a sensor 621 arranged in the center for regular reflection light which receives regular reflection light (R1), and a sensor 622 arranged in the periphery for diffusely reflected light to receive diffusely reflected light (R2). In this embodiment, sensor unit 600 can detect the quantity of regular reflection light by the image surface of the original (see FIG. 5A) and the quantity of light diffusely reflected by the surface (see FIG. 5B). Based on the two kinds of quantities of light, the quantity related to the glossiness of the image surface of the original is detected. The quantity related to the glossiness of the image surface of the original based on these two kinds of the quantities of light will be now descried.

Figure 6A:
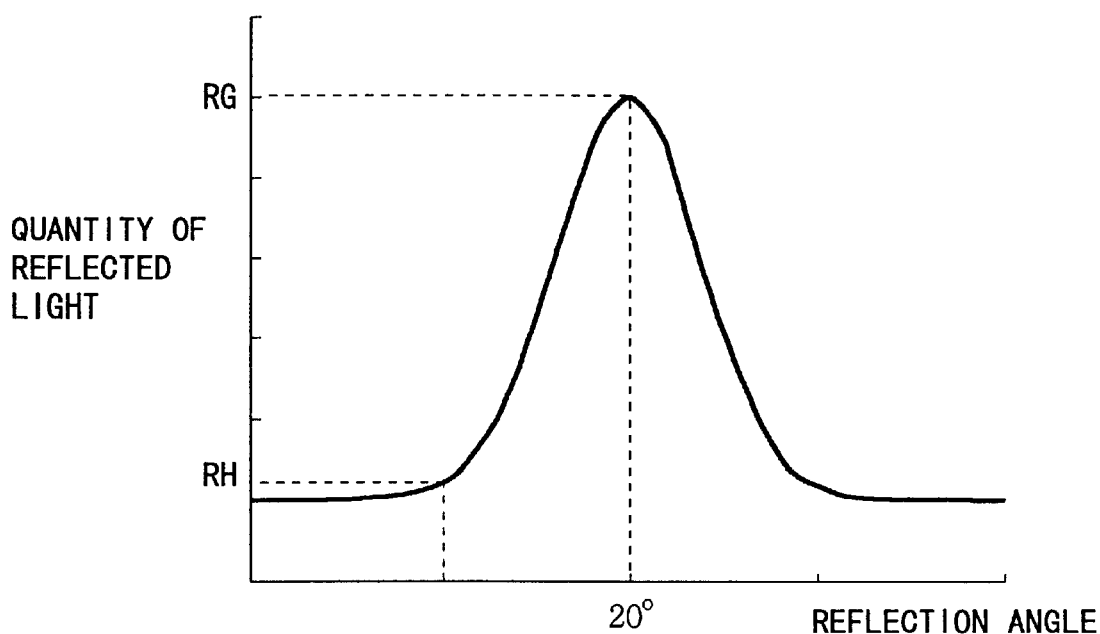
FIGS. 6A and 6B are graphs each showing a general reflected light quantity distribution relative to an reflection angle of the image surface of an original.
Figure 6B:
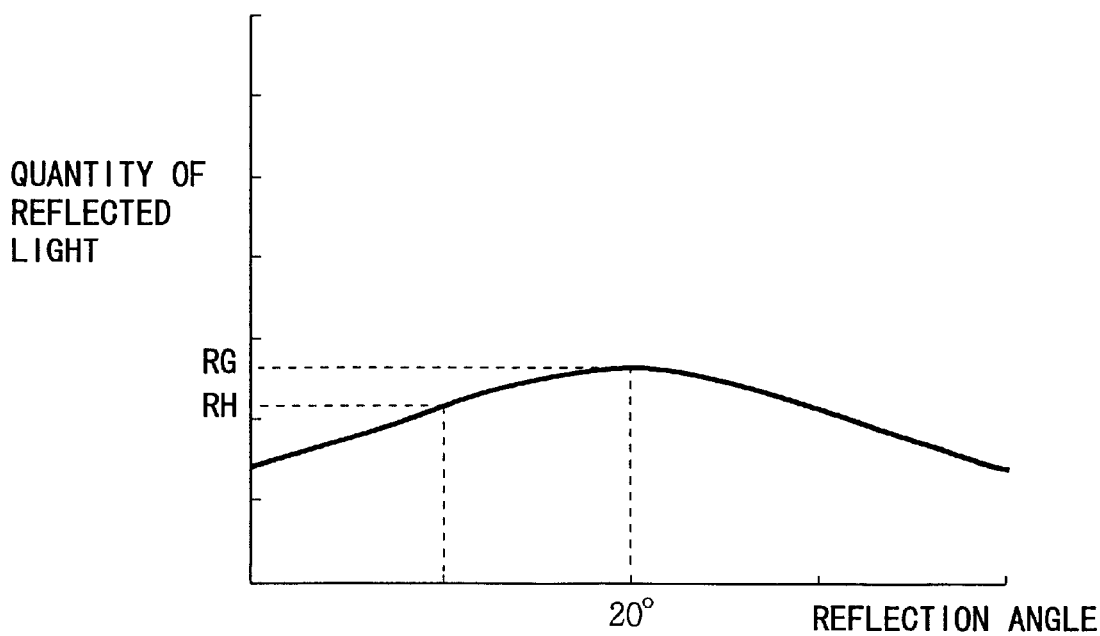

FIGS. 6A and 6B each show a typical distribution of quantity of light for the reflection angle of the image surface of an original when the angle of incidence is 20°. Note that FIG. 6A corresponds to the case in which the image surface of the original is smooth, in other words, the glossiness is relatively high, and FIG. 6B corresponds to the case in which the image surface of the original is rough, in other words, the glossiness is relatively low. In the figures, RG represents the quantity of a regular reflection light component as detected by sensor 621, while RH represents the quantity of a light diffusely reflected light component as detected by sensor 622 for diffusely reflected light.

Referring to FIG. 6A, if the glossiness of the image surface of the original is high, the ratio of regular reflection light in the reflected light is large, and therefore a steep peak is present around the reflection angle of 20° in the reflection light quantity distribution. More specifically, the ratio of the quantity of regular reflection light RG is very large, and the ratio of the quantity of diffusely reflected light RH therearound is small.

Meanwhile, referring FIG. 6B, if the glossiness of the image surface of the original is low, the ratio of a diffusely reflected light component is large in the reflected light, and a peak present around the reflection angle of 20° is gentle as compared to the high glossiness case.

As a result, in the reflected light quantity distribution, if RG/RH (the ratio of regular reflection light quantity RG and diffusely reflected light quantity RH) can be calculated, the state of the image surface of the original, in other words, the degree of the glossiness of the image surface of the original is available. More specifically, RG/RH represents the quantity related to the glossiness of the image surface of the original.

Figure 7:
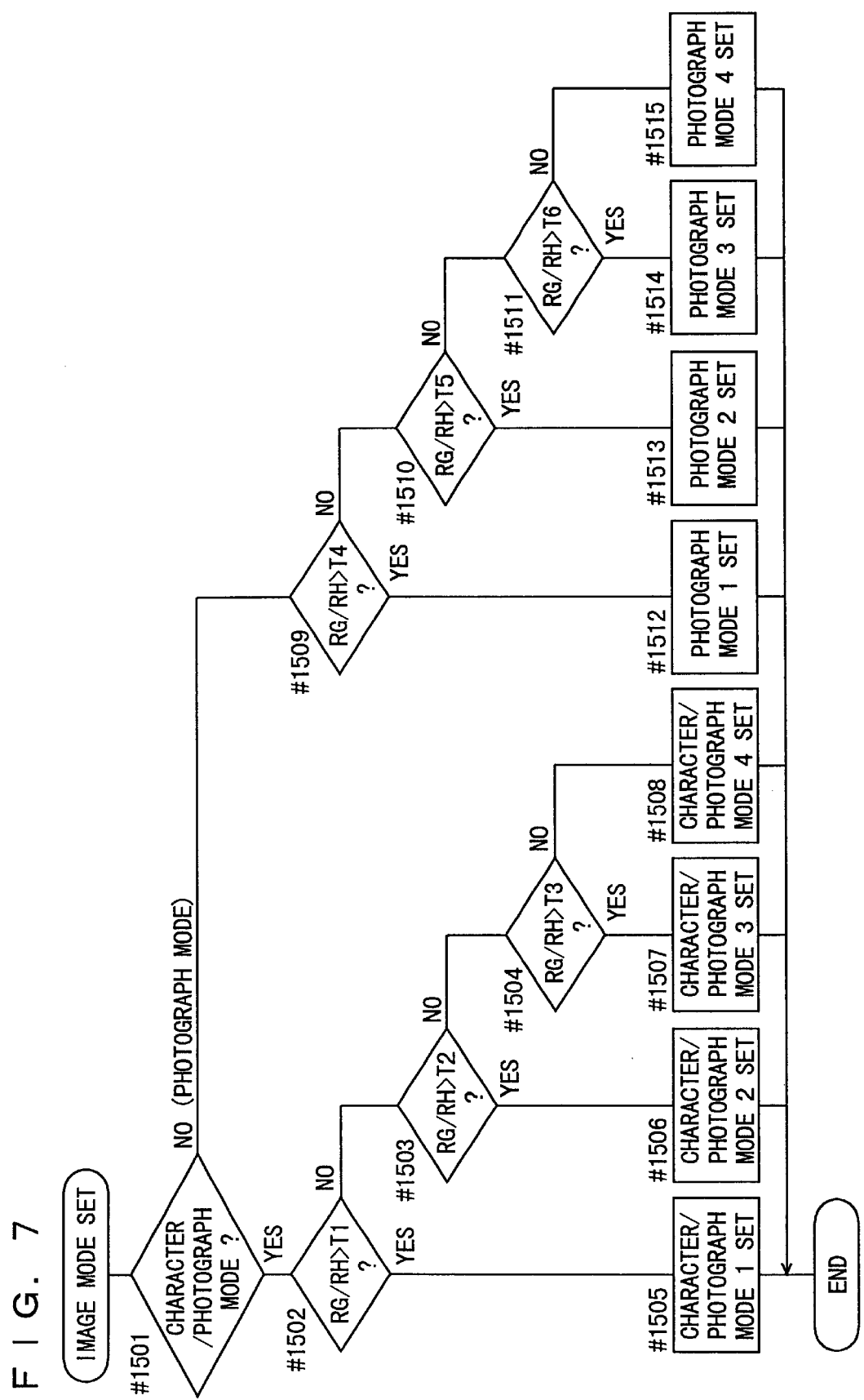
FIG. 7 is a flow chart for use in illustration of a sub routine in an image mode setting processing in FIG. 4.

Note that in this embodiment, in the image mode setting step in #15, RG/RH is used to determine the image mode. FIG. 7 is a flow chart for use in illustration of a sub routine in the image mode setting step.

In the image mode setting step, it is determined in #1501 if the copy mode has been set to the "character/photograph mode". If the character/photograph mode has been set, it is determined if RG/RH is greater than T1 in #1502. If RG/RH is not more than T1, it is determined in #1503 if RG/RH is greater than T2. If RG/RH is not more than T2, it is determined in #1504 if RG/RH is greater than T3.

If RG/GH>T1, the image mode is set to the "character/photograph mode 1" (#1505). If T2<RG/RH≦T1, the image mode is set to the "character/photograph mode 2" (#1506). If T3<RG/RH≦T2, the image mode is set to the "character/photograph mode 3" (#1507). If RG/RH≦T3, the image mode is set to the "character/photograph mode 4" (#1508). Note that T1 to T3 are predetermined threshold values and T1>T2>T3 holds.

Meanwhile, if it is determined in #1501 that the image mode is not the "character/photograph mode", more specifically if the image mode is the "photograph mode", it is determined in #1509 if RG/RH is greater than T4. If RG/RH is not more than T4, it is determined in #1510 if it is greater than T5. If RG/RH is not more than T5, it is determined in #1511 if it is greater than T6.

If RG/RH>T4, the image mode is set to the "photograph mode 1" (#1512). If T5<RG/Rh≦T4, the image mode is set to the "photograph mode 2" (#1513). If T6<RG/RH≦T5, the image mode is set to the "photograph mode 3" (#1514). If GR/RH≦T6, the image mode is set to the "photograph mode 4" (#1515). Note that T4 to T6 are predetermined threshold values, and T4>T5>T6 holds.

As described above, in this embodiment, the copy mode selected by operation panel 90 and the state of the image surface of an original (the value of RG/RH) are taken into consideration, and an appropriate image mode (character/photograph modes 1 to 4 or photograph modes 1 to 4) is set.

Note that the image mode includes information on other image forming conditions set in operation panel 90 (such as copy mode, original mode, exposure level, copy magnification, and recording sheet size). The information on these other image forming conditions in each image mode are, however, as has been set by operation panel 90, in other words, the information is not used to determine the image mode in combination with the other condition, i.e., the glossiness of the image surface of the original such as the copy mode, no additional detailed description is provided herein.

Also, as described above, according to the present embodiment, if the "character/photograph mode" or the "photograph mode" is selected as the copy mode, one image mode of the four image mode, i.e., the "character/photograph modes 1 to 4" or "photograph modes 1 to 4" is selected depending upon the value of RG/RH. Thus, image data may be produced more based on the sate of the image surface of the original than conventional techniques according to which the image mode is selected based on whether the value of RG/RH is greater than a prescribed threshold value, in other words, than the case in which one image mode is selected from two image modes. Note that according to the present embodiment, the number of selectable image modes is 4 for one copy mode, but the invention is not limited to this, and a larger number of image modes can be selected depending upon the capacity of the memory provided at overall control portion 100.

4. Production of Image Data

Figure 8:
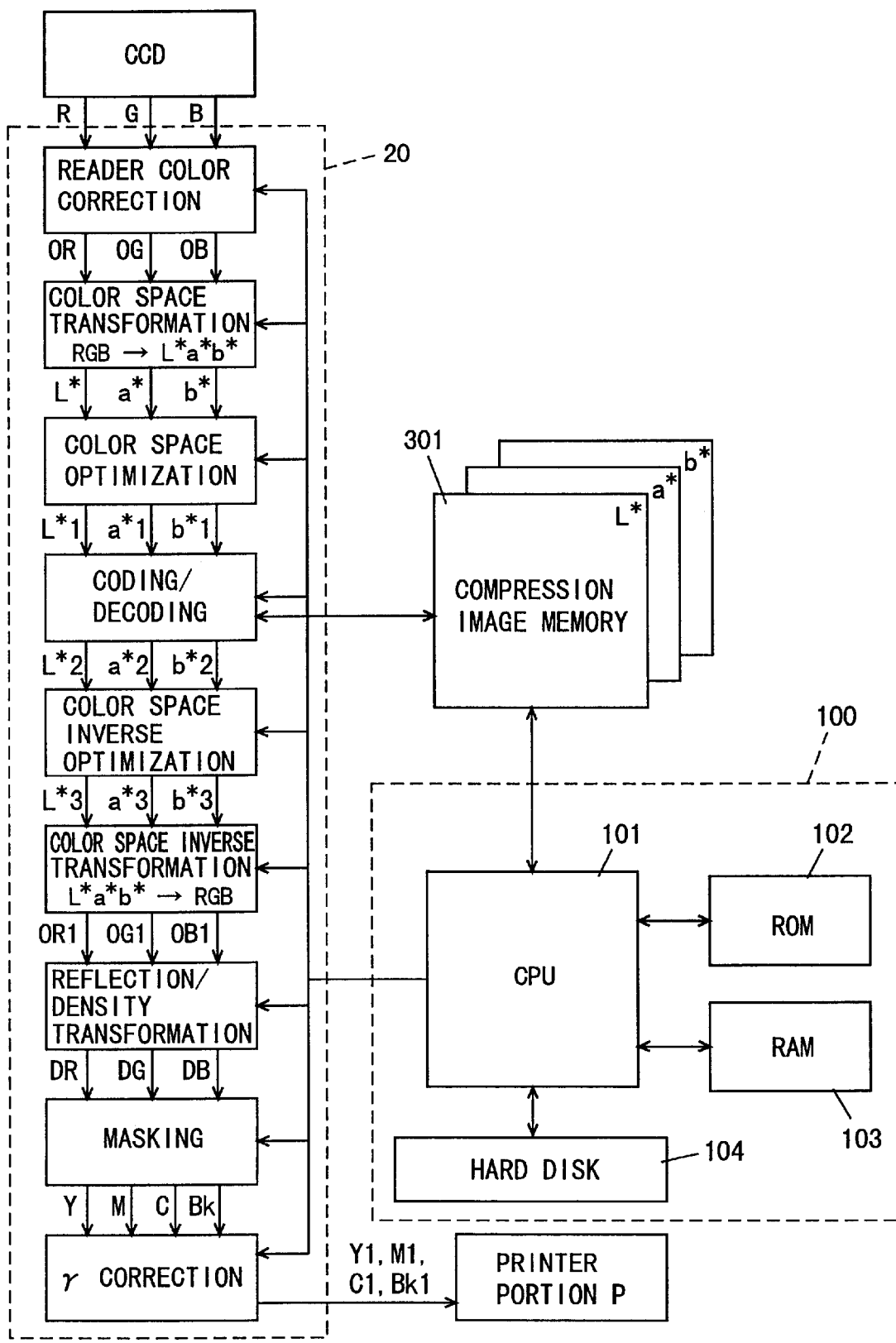
FIG. 8 is a diagram for use in illustration of how image data read by CCD forming a line sensor is transformed in the copying machine in FIG. 1.
Figure 10A:
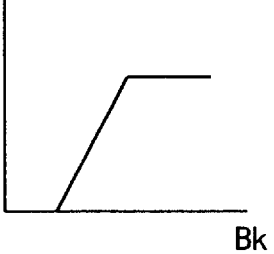
FIGS. 10A to 10D are graphs showing transform functions $F911Bk$ to $F914Bk$ used in $\gamma$ correction to image data in the copying machine in FIG. 1 by way of illustration.
Figure 10B:
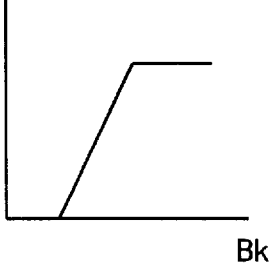
Figure 10C:
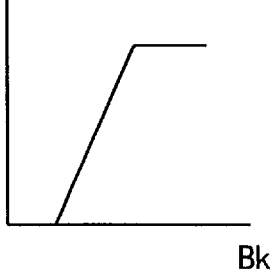
Figure 10D:
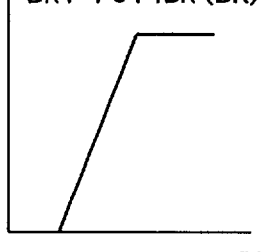
Figure 11A:
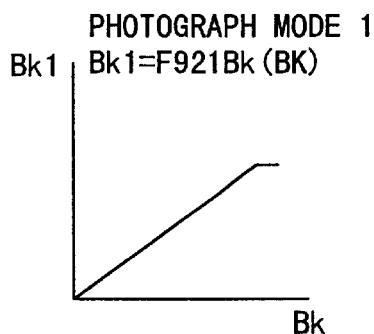
FIGS. 11A to 11D are graphs showing transform functions $F921Bk$ to $F924Bk$ used in $\gamma$ correction to image data in the copying machine in FIG. 1 by way of illustration.
Figure 11B:
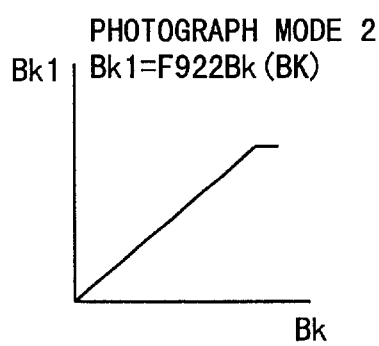
Figure 11C:
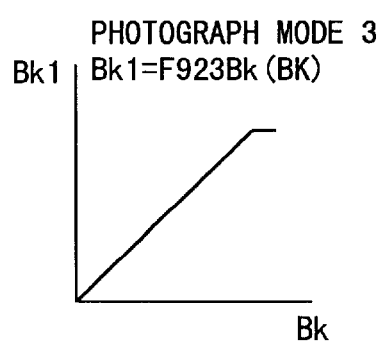
Figure 11D:
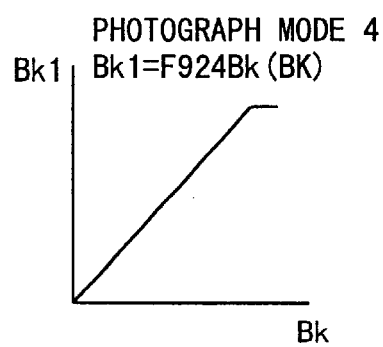

Referring to FIG. 8, the image processing step in #19 will be now descried. The image processing step is controlled by overall control portion 100, and performed in image processing unit 20. In the image processing step, image data (R, G, B) read by the CCDs forming line sensor 7 is converted into data to be input to printer portion P. Each processing step in the image processing will be now sequentially described.

Reader color correction processing

Incident light to line sensor 17 having an arrangement of a number of CCDs is photoelectrically converted to obtain electrical signals R,G and B. Electrical signals R, G and B are converted into standard RGB data, OR, OG, OB (standardized in NTSC or Hi-Vision format) so that the signals can be more readily handled in the following processing. Data OR, OG and OB are represented by the following expression (1).

$$OR=F1R(R, G, B)$$
$$OG=F1G(R, G, B)$$
$$OB=F1B(R, G, B) \quad (1)$$

wherein transformation functions F1R, F1G and F1B are produced by multiplying arguments R, G and B by factors respectively determined for the arguments, and adding the multiplied R, G and B. For example, for F1R, the factor for argument R is the largest and the factors for arguments G and B are smaller.

Color space transformation processing

OR, OG and OB data is transformed into $L^*a^*b^*$ color space data. These pieces of data are transformed into $L^*a^*b^*$ data, because the $L^*a^*b^*$ data can be coded with relatively small image degradation and is advantageous in exchanging color image data between a plurality of apparatuses. The $L^*a^*b^*$ data is expressed as follows:

$$L^*=F2L(OR, OG, OB)$$
$$a^*=F2a(OR, OG, OB)$$
$$b^*=F2b(OR, OG, OB) \quad (2)$$

wherein transformation functions F2L, F2a and F2b are used to transform input data OR, OG and OB into data in the XYZ standard colorimetiic system according to transformation formulas determined by the NTSC standard or HI-Vision standard and then into the $L^*a^*b^*$ colorimetric system.

Color space optimization processing

In order to minimize degradation in the picture quality in the succeeding coding/decoding processing, $L^*$, $a^*$, and $b^*$ are transformed into the $L^*1$, $a^*1$, and $b^*1$ by optimizing the color space. $L^*1$, $a^*1$, and $b^*1$ can be expressed as follows:

$$L^*1=F3L(L^*)$$
$$a^*1=F3a(L^*, a^*)$$
$$b^*1=F3b(L^*, b^*) \quad (3)$$

wherein transformation functions F3L, F3a. and F3b are functions used to linearly transform input data $L^*$, $a^*$ and $b^*$, and therefore data $L^*1$, $a^*1$ and $b^*1$ resulting from the transformation will no longer have color information.

Coding/decoding processing

Data $L^*1$, $a^*1$ and $b^*1$ is coded according to the block truncation coding and stored in a compression image memory 301, and conversely the coded data in compression image memory 301 is decoded to produce image data $L^*2$, $a^*2$ and $b^*2$. Since the block truncation coding/decoding is irreversible and therefore input data $L^*1$, $a^*1$ and $b^*1$ and $L^*2$, $a^*2$ and $b^*2$ will be slightly different data. Herein, compression image memory 301 is included in memory unit 30. $L^*2$, $a^*2$ and $b^*2$ can be expressed as follows:

$$L^*2=F4L(L^*1)$$
$$a^*2=F4a(a^*1)$$
$$b^*2=F4b(b^*1) \quad (4)$$

wherein transformation functions F4L, F4a and F4b are not predetermined functions and represent degradation in data When coding/decoding is performed, and the functions vary depending upon the distribution of peripheral data. More specifically, the functions are available only when coding/decoding is performed.

Color space inverse optimization processing

A processing of transforming $L^*2$, $a^*2$ and $b^*2$ into $L^*3$, $a^*3$ and $b^*3$ is performed. This processing is entirely opposite to the processing performed in the "color space optimization processing." $L^*3$, $a^*3$ and $b^*3$ can be expressed as follows:

$$L^*3=F5L(L^*2)$$
$$a^*3=F5a(L^*2, a^*2)$$
$$b^*3=F5b(L^*2, b^*2) \quad (5)$$

wherein transformation functions F5L, F5a and F5b are the inverse functions of F3L, F3a and F3b. By this processing, data $L^*3$, $a^*3$ and $b^*3$ resulting from the inverse transformation correspond to data $L^*$, $a^*$ and $b^*$ before the color space optimization processing, which means that the data representing the color information is once again obtained.

Color space inverse transformation processing

A processing of transforming decoded data $L^*3$, $a^*3$ and $b^*3$ into data (OR1, OG1, OB1) corresponding to the previously described data OR, OG and OB. Since data has been degraded in the processings until this point, OR1, OG1 and OB1 are not necessarily the same as OR, OG and OB. Data OR1, OG1 and OB1 are expressed as follows:

$$OR1=F6R(L^*3, a^*3\ b^*3)$$
$$OG1=F6G(L^*3, a^*3\ b^*3)$$
$$OB1=F6B(L^*3, a^*3\ b^*3) \quad (6)$$

wherein transformation functions F6R, F6G and F6B are the inverse functions of F2L, F2a and F2b.

Reflection/density transformation processing

OR1, OG1 and OB1 described above will be now transformed into density data DR, DG and DB. Density data DR, DG and DB can be expressed as follows:

$$DR=F7R(OR1)$$
$$DG=F7G(OG1)$$
$$DB=F7G(OG1) \quad (7)$$

wherein transformation functions F7R, F7G and F7b are logarithms.

Masking processing

In order to print data with printer portion P, density data DR, DG and DB are transformed into data of toner colors, C, M, Y and Bk used in a full color copying machine. Herein C, M, Y and Bk are expressed as follows. Note that C, M, Y and Bk resulting from this processing differ depending upon an image mode set in #15 or #16.

Character mode $$Y=F801Y(DR, DG, DB)$$
$$M=F801M(DR, DG, DB)$$
$$C=F801C(DR, DG, DB)$$
$$Bk=F801Bk(DR, DG, DB) \qquad (8)$$

Character/photograph mode 1

$$Y=F811Y(DR, DG, DB)$$
$$M=F811M(DR, DG, DB)$$
$$C=F811C(DR, DG, DB)$$
$$Bk=F811Bk(DR, DG, DB) \qquad (9)$$

Character/photograph mode 2

$$Y=F812Y(DR, DG, DB)$$
$$M=F812M(DR, DG, DB)$$
$$C=F812C(DR, DG, DB)$$
$$Bk=F812Bk(DR, DG, DB) \qquad (10)$$

Character/photograph mode 3

$$Y=F813Y(DR, DG, DB)$$
$$M=F813M(DR, DG, DB)$$
$$C=F813C(DR, DG, DB)$$
$$Bk=F813Bk(DR, DG, DB) \qquad (11)$$

Character/photograph mode 4

$$Y=F814Y(DR, DG, DB)$$
$$M=F814M(DR, DG, DB)$$
$$C=F814C(DR, DG, DB)$$
$$Bk=F814Bk(DR, DG, DB) \qquad (12)$$

Photograph mode 1

$$Y=F821Y(DR, DG, DB)$$
$$M=F821M(DR, DG, DB)$$
$$C=F821C(DR, DG, DB)$$
$$Bk=F821Bk(DR, DG, DB) \qquad (13)$$

Photograph mode 2

$$Y=F822Y(DR, DG, DB)$$
$$M=F822M(DR, DG, DB)$$
$$C=F822C(DR, DG, DB)$$
$$Bk=F822Bk(DR, DG, DB) \qquad (14)$$

Photograph mode 3

$$Y=F823Y(DR, DG, DB)$$
$$M=F823M(DR, DG, DB)$$
$$C=F823C(DR, DG, DB)$$
$$Bk=F823Bk(DR, DG, DB) \qquad (15)$$

Photograph mode 4

$$Y=F824Y(DR, DG, DB)$$
$$M=F824M(DR, DG, DB)$$
$$C=F824C(DR, DG, DB)$$
$$Bk=F824Bk(DR, DG, DB) \qquad (16)$$

Transformation functions F811Y to F824Y, F811M to F824M, F811C to F824C and F811Bk to F824Bk are produced by multiplying respective arguments DR, DG, and DB by predetermined factors and added, and a set of functions is selected for use depending upon a set image mode. For example, an image on an original surface with high level glossiness such as photographic paper is generally printed to be bluish as compared to other kinds of images.

In copying machine 1, when an image formed on such an original surface with high level glossiness like printing paper, the user can set a character/photograph mode or a photograph mode as a copy mode. If a character/photograph mode or a character mode is set as the copy mode and the glossiness of the image surface is high, character/photograph mode 1 or photograph mode 1 is selected as an image mode.

Therefore, when a transformation function used for character/photograph mode 1 or photograph mode 1 is determined so that a resulting print will not be bluish, the user does not have to adjust the picture quality into details every time and good picture quality is obtained automatically.

γ correction

γ correction is performed to YMCBk data in order to linearly reproduce the printing density, and the produced data is sent to printer portion P as Y1, M1, C1 and Bk1 through memory unit 30 (not shown in FIG. 8) for printing. Y1, M1, C1 and Bk1 are expressed as follows. Note that data C1, M1, T1 and Bk1 obtained by this processing varies depending upon a set image mode.

Character mode $$Y1=F901Y(Y)$$
$$M1=F901M(M)$$
$$C1=F901C(C)$$
$$Bk1=F901Bk(Bk) \qquad (17)$$

Character/photograph mode 1

$$Y1=F911Y(Y)$$
$$M1=F911M(M)$$
$$C1=F911C(C)$$
$$Bk1=F911Bk(Bk) \qquad (18)$$

Character/photograph mode 2

$$Y1 = F912Y(Y)$$

$$M1 = F912M(M)$$

$$C1 = F912C(C)$$

$$Bk1 = F912Bk(Bk) \qquad (19)$$

Character/photograph mode 3

$$Y1 = F913Y(Y)$$

$$M1 = F913M(M)$$

$$C1 = F913C(C)$$

$$Bk1 = F913Bk(Bk) \qquad (20)$$

Character/photograph mode 4

$$Y1 = F914Y(Y)$$

$$M1 = F914M(M)$$

$$C1 = F914C(C)$$

$$Bk1 = F914Bk(Bk) \qquad (21)$$

Photograph mode 1

$$Y1 = F921Y(Y)$$

$$M1 = F921M(M)$$

$$C1 = F921C(C)$$

$$Bk1 = F921Bk(Bk) \qquad (22)$$

Photograph mode 2

$$Y1 = F922Y(Y)$$

$$M1 = F922M(M)$$

$$C1 = F922C(C)$$

$$Bk1 = F922Bk(Bk) \qquad (23)$$

Photograph mode 3

$$Y1 = F923Y(Y)$$

$$M1 = F923M(M)$$

$$C1 = F923C(C)$$

$$Bk1 = F923Bk(Bk) \qquad (24)$$

Photograph mode 4

$$Y1 = F924Y(Y)$$

$$M1 = F924M(M)$$

$$C1 = F924C(C)$$

$$Bk1 = F924Bk(Bk) \qquad (25)$$

Transformation functions F911Y to F924Y, F911M to F924M, F911C to F924C, F911Bk to F924Bk are used as a correction table for an experimentally obtained gradation curve, and a set of functions are selected for use depending upon a set image mode. For example, an image on a surface with high level glossiness such as printing paper is likely to be densely printed as compared to other kinds of images. Therefore, if a transformation function used when a character/photograph mode or a photograph mode is set as the copy mode and character/photograph mode 1 or photograph mode 1 used with high level glossiness is set as the image mode is set to one for printing thinly, while a transformation function used in character/photograph mode 4 or photograph mode 4 set with low level glossiness is set to one for printing densely, the user can automatically obtain good picture quality without having to adjust the picture quality into details point by point.

FIGS. 9, 10A to 10D and 11A to 11D show examples of transformation functions F901Bk, F911Bk to F914Bk and F921Bk to F924Bk for respective image modes. Note that the transformation function (γ curve) in each mode can be appropriately determined based on experiments or the like.

The processings described in conjunction with FIG. 8 are controlled by CPU 101 (FIG. 2) included in overall control portion 100. CPU 101 can set or change parameters or the like in each processing. Data in compression image memory 301 can be read and written by CPU 101. Processings performed by CPU 101 are written in a ROM 102, and parameters necessary during processings or buffers for calculation are read and written using a RAM 103. Recompressed data obtained by recompressing performed in CPU 101 is stored in a hard disk 104 which is a data storing device. ROM 102, RAM 103 and hard disk 104 are included in overall control portion 100.

5. Effect of Producing Image Data Depending Upon Glossiness

In the above-described embodiment, when a certain copy mode is set depending upon the glossiness of the image surface of a detected original (RG/RH), the image mode in the image processing is automatically selected, so that an appropriate copy based on the glossiness of the original can be obtained.

Figure 12:
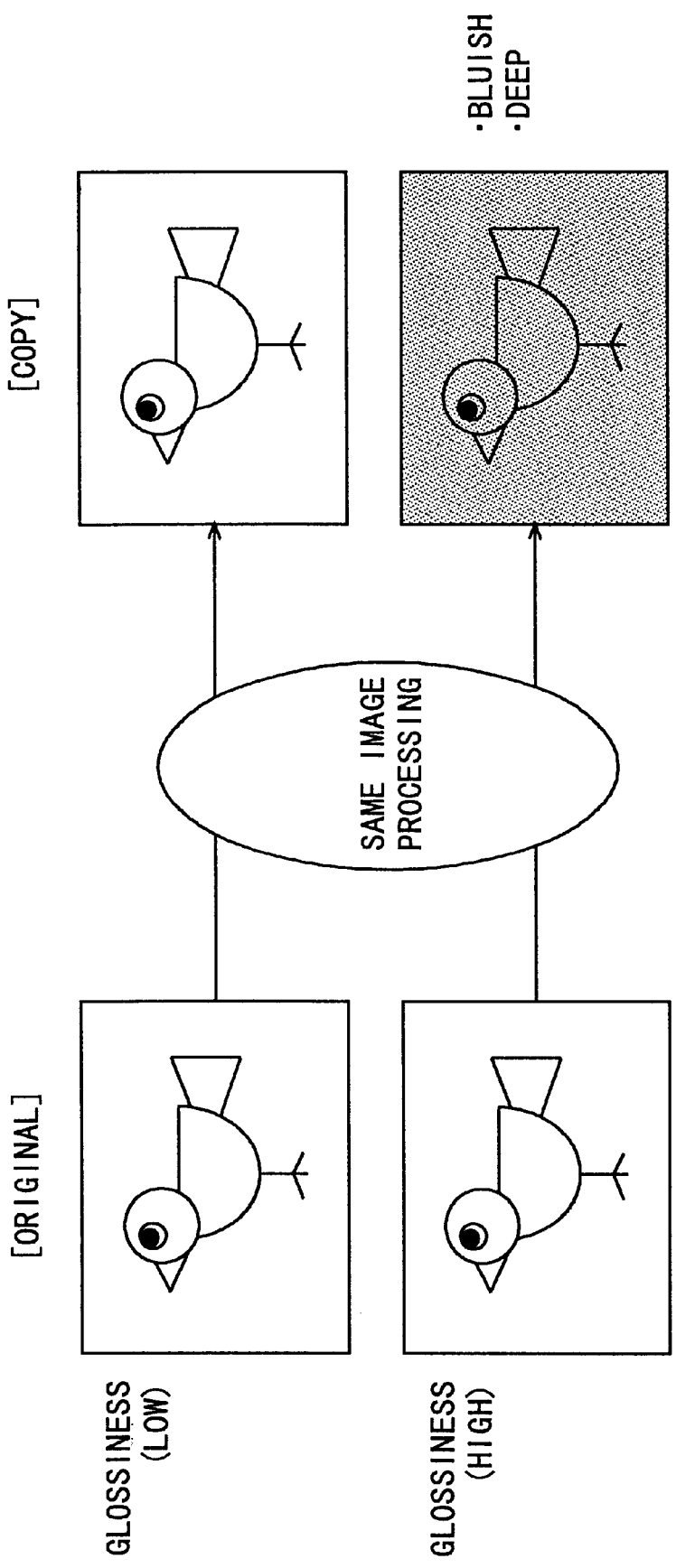
FIG. 12 is a schematic diagram showing the effect of automatically selecting a transform function at the time of processing an image according to the glossiness of the image surface of an original in a conventional copying machine.
Figure 13:
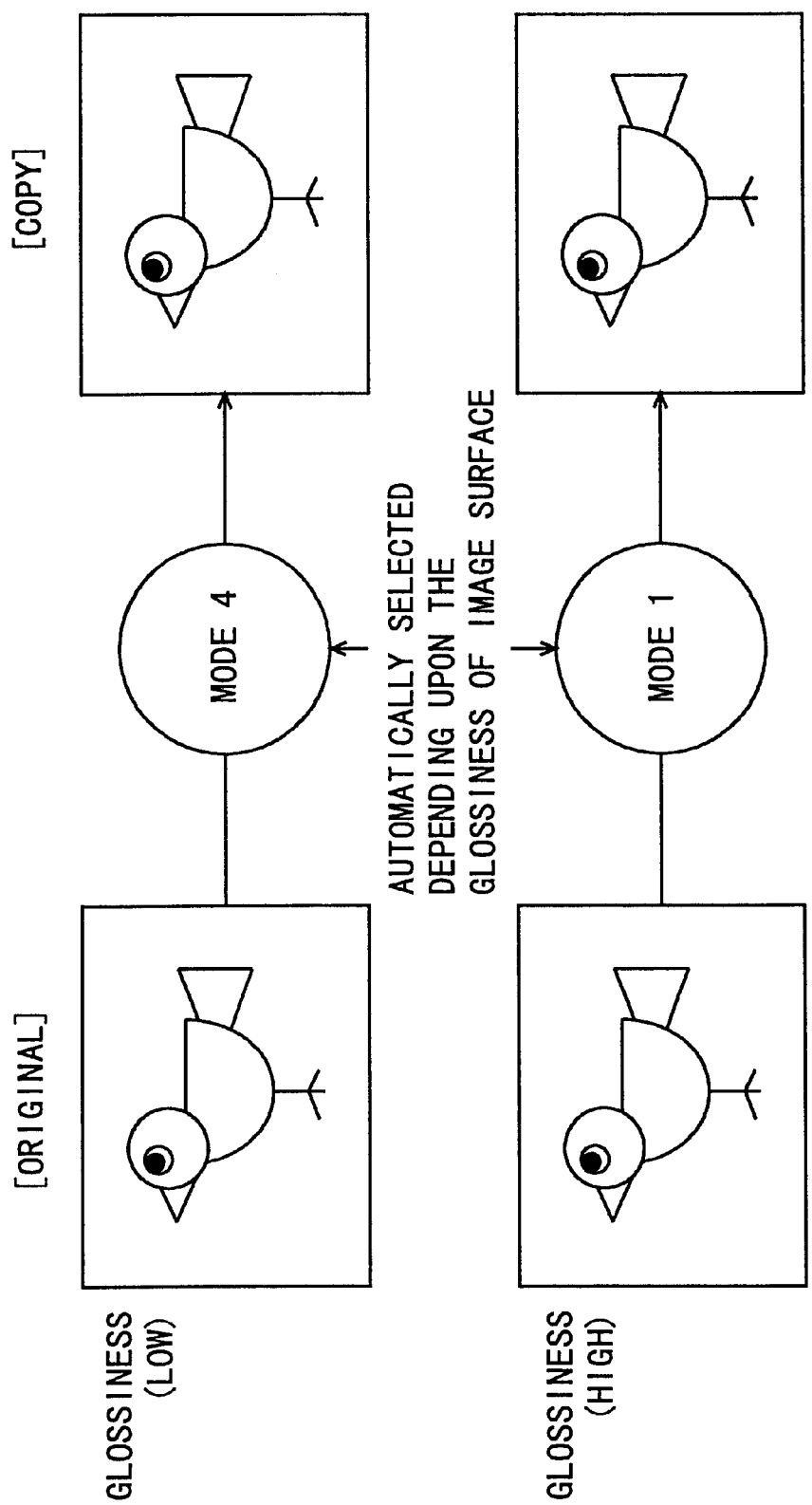
FIG. 13 is a schematic diagram showing the effect of automatically selecting a transform function at the time of processing an image according to the glossiness of the image surface of an original in the copying machine in FIG. 1.

FIGS. 12 and 13 are views for use in illustration of this effect of the embodiment.

FIG. 12 shows the effect of an image processing by a conventional copying machine.

Referring to FIG. 12, in a conventional machine, when a character/photograph mode or a photograph, mode is selected as a copy mode, image data must be uniformly processed in each mode irrespectively of the glossiness of the image surface of an original. An original without glossiness can be copied normally but an oiginal with glossiness can be copied to be bluish or generally into a dense color. By the conventional machine, when the character/photograph mode or photograph mode is selected, the image mode might be selected based on whether or not the value of RG/RH is greater than a threshold value, but even in such a case, the above-described disadvantage of the copied image is hardly solved.

FIG. 13 is a view for use in illustration of the effect of image processing in the copying machine according to the present embodiment.

Referring to FIG. 13, according to this embodiment, when a copy mode such as a character/photograph mode or a photograph mode is selected using operation panel 90, any of the image modes, character/photograph modes 1 to 4 or photograph modes 1 to 4 is selected depending upon the glossiness of the image surface of the original. Thus, the problem associated with a copy image when the glossiness of the image surface of an original is high which has been encountered in the conventional copying machine can be solved.

In this embodiment, the reflectance-density characteristic can be effectively corrected, so that transformation functions depending upon the state of the image surface of an original are prepared in the masking processing and γ correction processing, but the invention is not limited to this. In other processings such as the reflectance/density transformation processing, a transformation function depending upon the state of the image surface of an original may be prepared.

In the embodiment described above, sensor unit 600 which measures RG/RH and overall control portion 100 form glossiness detection means to detect the glossiness of the image surface of an original. Operation panel 90 forms input means to set conditions for forming images. There is provided control means to prohibit the operation of the glossiness detection means in producing image data when a character mode is selected as the copy mode (No in #13, see FIG. 4) and a prescribed image forming condition is set in the input means by overall control portion 100 to perform the image mode setting processing, without the step of detecting the state of the image surface of the original in #14. The copy mode can be set using operation panel 90, and therefore the input means can be formed by the panel. If a character mode is selected as the copy mode, overall control portion 100 which performs the image mode setting processing in #16 without the step of detecting the state of the image surface of an original in #14 forms the control means to control the operation of the glossiness detection means depending upon the image mode set by the input means.

According to the embodiment, overall control portion 100 which performs the image setting processing described in conjunction with FIG. 7 forms determination means to determine the image mode depending upon the detection output of the glossiness detection means and the set image forming conditions. The RG/RH forms the detection output of the glossiness detection means. As has been described in conjunction with FIG. 7, in the image mode setting processing, any of the image modes, character/photograph modes 1 to 4 or photograph modes 1 to 4 is determined depending upon the value of RG/RH, so that the determination means determines one kind of image modes from at least three kinds of prescribed image modes depending upon the detection output of the glossiness detection means.

Also according to this embodiment, as has been described in conjunction with FIG. 8, in the image processing (#19, see FIG. 4), the transformation functions used in the γ correction or masking processing are changed based on the value of RG/FH, and the image mode is changed depending upon the detection output of the glossiness detection means, so that the content of processing in the γ correction or color correction processing in producing image data is changed.

According to this embodiment, the glossiness is detected by detecting RG/RH, but the invention is not limited to this, and other methods to detect the degree of the glossiness of the image surface of an original may be employed.

6. Modification 1

In the above described embodiment, as shown in FIG. 4, when a "character mode" is selected as the copy mode using operation panel 90, the step of detecting the state of the image surface of an original (#14) is not performed, but whether or not to perform the step of detecting the state of the image surface of the original is determined not only based on the selected copy mode. It may be determined for example based on whether or not to use an automatic document feeder (ADF) such as original transport portion 500 set in operation panel 90.

Figure 14:
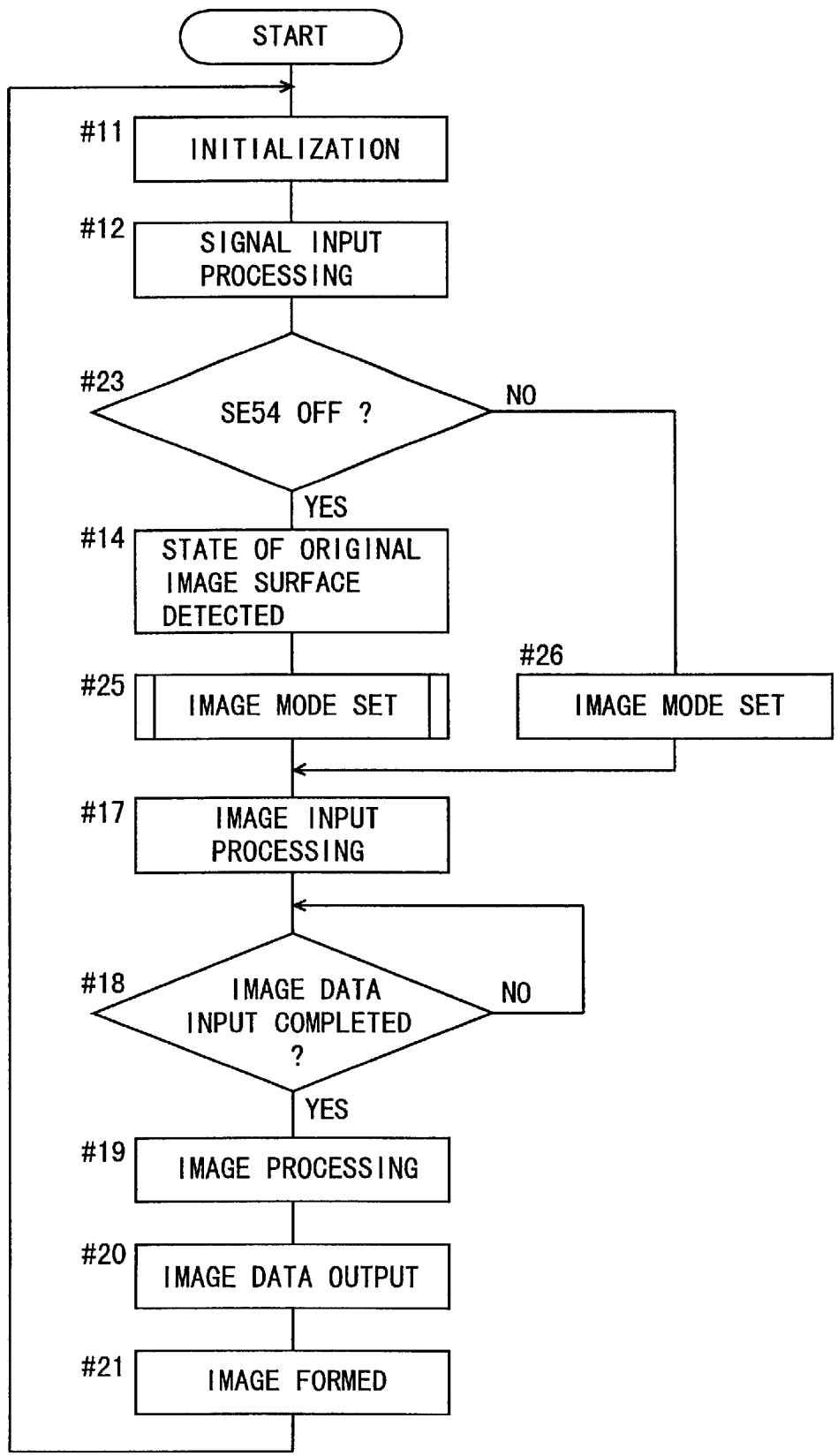
FIG. 14 is a flow chart for use in illustration of a modification of the processing content shown in FIG. 4.

FIG. 14 shows a modification as described above. In FIG. 14, the same steps as those in FIG. 4 are denoted by the same step numbers (such as #11), and additional description is not provided.

Referring to FIG. 14, in this modification, steps #13, #15 and #16 in FIG. 4 are replaced with steps #23, #25 and #26, respectively. It is determined in #23 whether or not the output of empty sensor SE54 about detection is off, in other words, whether or not an original is present on original feeding tray 510. If the output is off, in other words, there is no original on original feeding tray 510, the control proceeds to #14, and the step of detecting the state of the image surface of the original to calculate RG/RH and then to #25.

In #25, an image mode setting processing according to the result of detection of the state in #14 is performed. A sub routine of the image mode setting processing in #25 is shown in FIG. 15.

Figure 15:
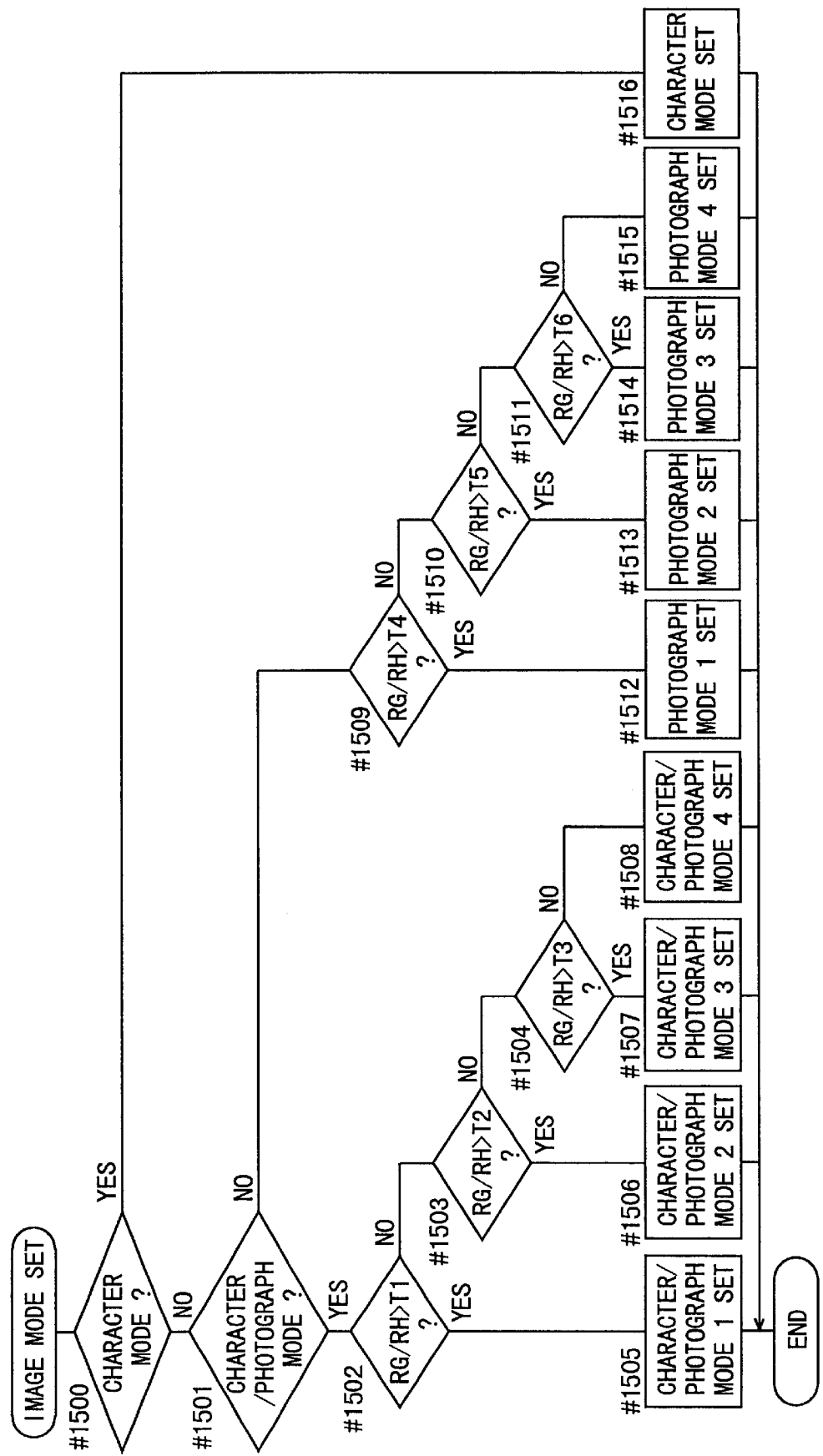
FIG. 15 is a flow chart showing a sub routine in the image mode set processing in FIG. 13.

Referring to FIG. 15, it is determined in #1500 whether a "character mode" is set as the copy mode by operation panel 90. If the character mode is set, the control proceeds to #1516, and a character mode is set as the image mode. If a character mode is not set, the control proceeds to #1501. In an image mode setting processing as shown in FIG. 15, steps #1501 to #1515 are the same as steps #1501 to 1515 in FIG. 7, and additional description is not provided.

Referring back to FIG. 14, in #23, if the detection output of empty sensor SE54 is not off, in other words, if an original is present on original feeding tray 510, step #14 is not performed and the control proceeds to #26 in which an image mode is set and then to #17.

In #26, if the copy mode is set to the "character/photograph mode" on operation panel 90, the image mode is set to "character/photograph mode 4", and if the copy mode is set to the "photograph mode", the image mode is set to "photograph mode 4". As a result, when the image mode is set in #26 and the copy mode is set to a "character/photograph mode" or "photograph mode", image data is produced irrespectively of the glossiness of the image surface of the original.

As in the foregoing, in modification 1 described in conjunction with FIGS. 14 and 15, the use of an ADF in a copying operation automatically causes detection of the state (glossiness) of the image surface of the original to be stopped. More specifically, if there is no need to detect the state of the image surface of an original, detection of the state of the image surface is no longer performed.

This eliminates the disadvantage that time for detecting the state of the image surface is included in producing image data even when detection of the image surface is not necessary, which necessitates wasteful long period of time for producing image data.

Whether or not to detect the state of the image surface of an original is determined based on whether or not to use an ADF for the following reason. More specifically, as described using FIGS. 12 and 13, a copied image becomes bluish when the glossiness of the image surface of an original is high. More specifically, if the glossiness of the image surface could be high, the state (glossiness) will have to be detected. However, when an ADF is used, the glossiness of the image surface of an original is generally low. In this embodiment, the state of the surface of an original is not detected assuming that the glossiness of the image surface is low when the user uses an ADF.

By modification 1 as described above, when it is set as an image forming condition that an original is transported using an automatic document feeder, the control means prohibits the operation of the glossiness detecting means.

7. Modification 2

Figure 16:
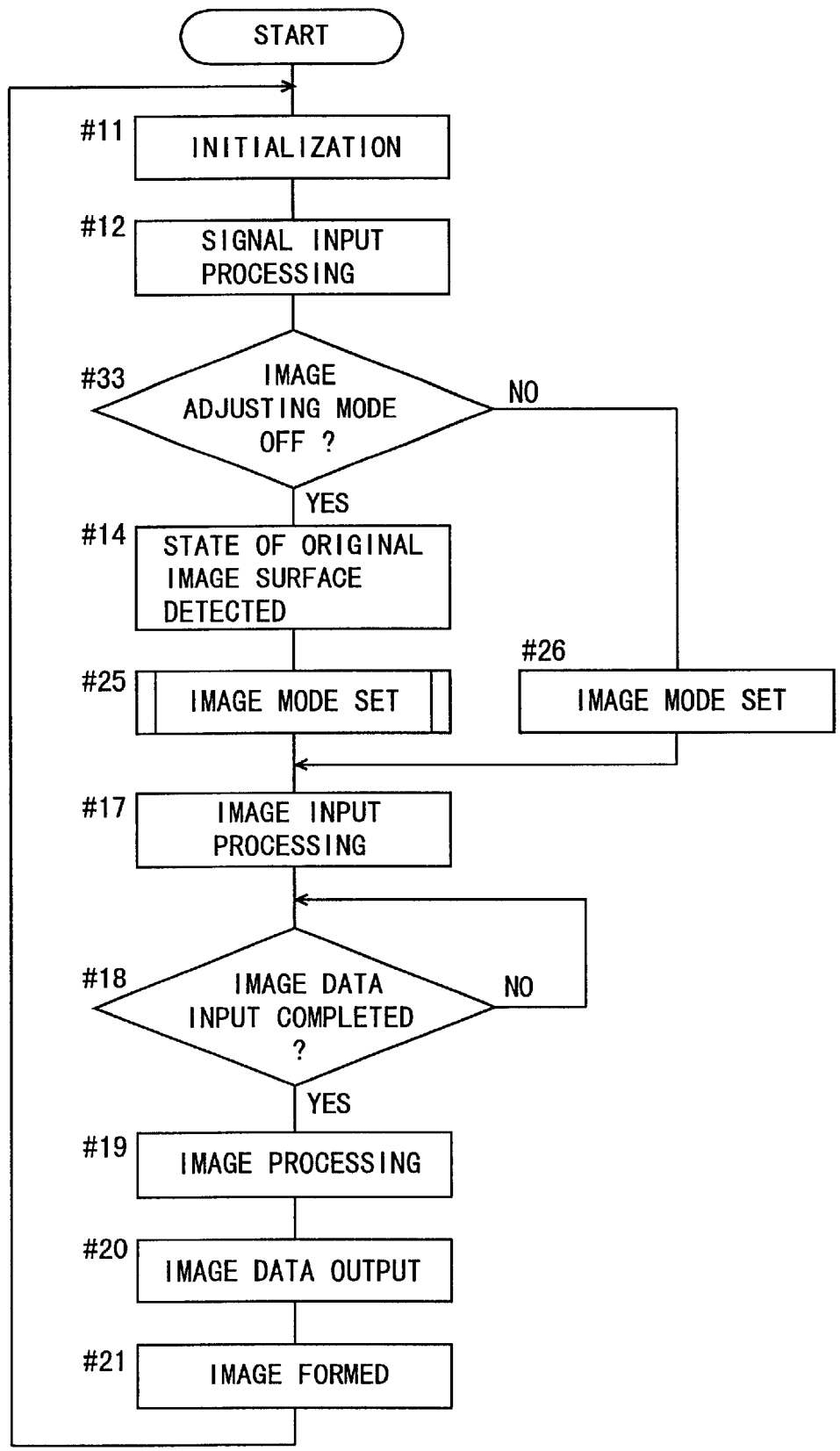
FIG. 16 is a diagram for use in illustration of another modification of the processing content shown in FIG. 14.

Copying machine 1 can select an image adjusting mode such as color adjustment and density adjustment using operation panel 90. Whether or not to detect the state of the image surface of an original (#14) may be determined based on whether or not the image adjustment mode has been selected. FIG. 16 shows such a modification of FIG. 4. Note that in FIG. 16, the same step numbers are used for the same steps as those in FIG. 4, and additional description is not provided.

Referring to FIG. 16, in this modification, steps #13, #15 and #16 are replaced by steps #33, #25, and #26, respectively.

In #33, whether or not the image mode is off, in other words, whether or not the image adjustment mode has been selected is determined. If the image adjustment mode is off, in other words, the image adjustment mode has not been selected, the control proceeds to #14, and the processing of detecting the state of the image surface of an original to calculate RG/RH is performed, and then control proceeds to #25. The content of step #25 is the same as the step in modification 1 (the same as step #25 in FIG. 14), and therefore additional description is not provided.

Meanwhile, if the image adjustment mode is not off in #33, in other words, if it is determined that the image adjustment mode such as color adjustment and density adjustment has been selected, the control proceeds to #26 and then to #17. Note that the content of step #26 is the same as that in modification 1 (the same as #26 in FIG. 14), and therefore additional description is not provided.

In modification 2 described in conjunction with FIG. 16, when the image adjustment mode is set in a copying machine, the state of the image surface of the original is automatically stopped to be detected. The user generally does not like automatic image correction by copying machine 1, when the image adjustment mode such as color adjustment and density adjustment is selected. Therefore, in modification 2, in such a case where the user does not usually desire automatic image correction using a machine, the processing time in a copying operation can be reduced.

In modification 2 as described above, when a condition for picture quality adjustment is set for image data to be produced as an image forming condition, the control means prohibits the operation of the glossiness detection means.

8. Modification 3

Figure 17:
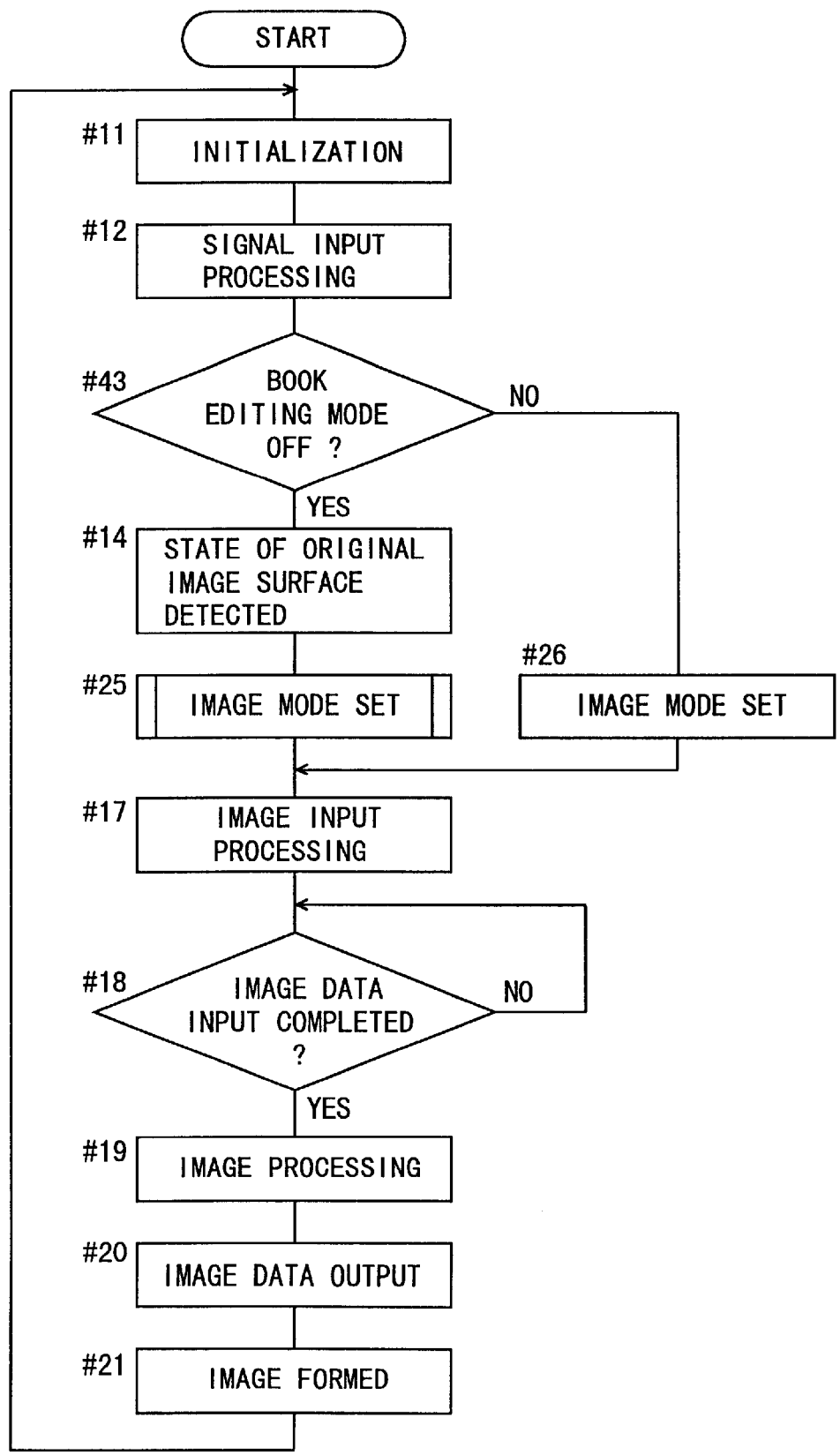
FIG. 17 is a diagram for use in illustration of another modification of the processing content shown in FIG. 4.

Copying machine 1 can select a "book editing mode" using panel 90. This book editing mode is a mode in which both right and left pages of bound original sheets placed on platen glass 19 are copied separately on different sheets. FIG. 17 shows such a modification of FIG. 4. In FIG. 17, the same steps as those in FIG. 4 are denoted with the same step numbers and additional description is not provided.

Referring to FIG. 17, in this modification, steps #13, #15 and #16 are replaced by steps #43, #25 and #26, respectively.

It is determined in #43 if the above described editing mode is off using operation panel 90, in other words, the book editing mode has not been selected. If the book editing mode is off, in other words, the book editing mode is not selected, the control proceeds to #14 and the state of the image surface of an original to detect RG/RH is detected, and then the control proceeds to #25. The content of # 25 is the same as that in modification 1 (#25 in FIG. 14), and therefore additional description is not provided.

Meanwhile, if it is determined in #43 that the book editing mode is not off, in other words, the book editing mode has been selected, the control proceeds to #26, and then to #17. Since the processing in #26 is the same as that in modification 1 (#26 in FIG. 14), additional description is not provided.

In modification 3 as described in conjunction with FIG. 17, when the book editing mode is selected, detection of the state of the image surface of the original is automatically omitted.

If the original is bound original sheets or the like, it is highly unlikely that the original is printing paper with high level glossiness on its image surface. Therefore, in modification 3, if there is little possibility that the image surface is formed by printing paper with high level glossiness like the case in which the book editing mode is selected, the state of the image surface of an original is not detected, and therefore time required for processing in a copying operation can be reduced.

In modification 3 as described above, when the use of bound original sheets is set as an image forming condition in the input means, the control means prohibits the operation of the glossiness detecting means.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An image reading apparatus to produce image data, comprising:

a light source and light sensor for detecting the glossiness of an image surface of an original;

a processing unit for prohibiting the operation of said glossiness detection means; and an input device for setting an image forming condition;

said processing unit prohibiting the light source and the light sensor from detecting the glossiness in producing said image data when a prescribed image forming condition is set in said input device.

2. An image reading apparatus comprising:

glossiness detection means for detecting the glossiness of an image surface of an original;

control means for prohibiting the operation of said glossiness detection means; and input means for setting an image forming condition;

said control means prohibiting the operation of said glossiness detection means in producing said image data when a prescribed image forming condition is set in said input means.

3. The image reading apparatus according to claim 2, further comprising determination means for determining an image mode depending upon the detection output of said glossiness detection means and said set image forming condition, for reading the image information of an original, and for producing image data based on the image information and said image mode, and said determination means determining one kind of image modes among at least three kinds of predetermined image modes based on said detection output.

4. The image reading apparatus according to claim 3, wherein the producing of the image data by said image reading means includes $\gamma$ correction or color correction processing, and said image mode is changed based on the detection output of said glossiness detection means, so that the content of processing in said $\gamma$ correction or said color correction is changed.

5. The image reading apparatus according to claim 2, wherein said control means prohibits the operation of said glossiness detection means when the use of an automatic document feeder for transporting an original is set as said image forming condition.

6. The image reading apparatus, according to claim 2, wherein said control means prohibits the operation of said glossiness detection means when a condition to adjust the picture quality of said image data to be produced is set as said image forming condition.

7. The image reading apparatus, according to claim 2, wherein said control means prohibits the operation of said glossiness detection means when a condition to use bound original sheets is set as said image forming condition.

8. An image reading apparatus, comprising:

glossiness detection means for producing image data based on an image mode and detecting the glossiness of the image surface of an original;

control means for prohibiting the operation of said glossiness detection means; and input means for setting an image mode, said control means controlling the operation of said glossiness detection means based on an image mode set by said input means.

* * * * *